United States Patent
Cuomo

(10) Patent No.: US 11,298,682 B2
(45) Date of Patent: Apr. 12, 2022

(54) ACTIVATED METAL LOW TEMPERATURE REACTION PROCESSES AND PRODUCTS

(71) Applicant: North Carolina State University, Raleigh, NC (US)

(72) Inventor: Jerome J. Cuomo, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 15/311,079

(22) PCT Filed: May 7, 2015

(86) PCT No.: PCT/US2015/029699
§ 371 (c)(1),
(2) Date: Nov. 14, 2016

(87) PCT Pub. No.: WO2015/175314
PCT Pub. Date: Nov. 19, 2015

(65) Prior Publication Data
US 2017/0080405 A1    Mar. 23, 2017

Related U.S. Application Data

(60) Provisional application No. 61/991,942, filed on May 12, 2014.

(51) Int. Cl.
| | |
|---|---|
| *C01B 31/02* | (2006.01) |
| *B01J 23/14* | (2006.01) |
| *C01B 21/02* | (2006.01) |
| *C01B 17/04* | (2006.01) |
| *C07C 7/12* | (2006.01) |
| *H01M 12/06* | (2006.01) |
| *C01B 32/05* | (2017.01) |
| *C01B 3/08* | (2006.01) |
| *C01F 7/42* | (2022.01) |
| *C01F 11/18* | (2006.01) |
| *C10L 3/10* | (2006.01) |

(52) U.S. Cl.
CPC ............ *B01J 23/14* (2013.01); *C01B 3/08* (2013.01); *C01B 17/04* (2013.01); *C01B 21/02* (2013.01); *C01B 32/05* (2017.08); *C01F 7/42* (2013.01); *C01F 11/18* (2013.01); *C07C 7/12* (2013.01); *H01M 12/06* (2013.01); *C10L 3/103* (2013.01)

(58) Field of Classification Search
CPC ...................................................... C01B 32/05
See application file for complete search history.

(56) References Cited

U.S. PATENT DOCUMENTS

| | | | | | |
|---|---|---|---|---|---|
| 3,920,800 | A | * | 11/1975 | Harris ................ | C01F 11/181 |
| | | | | | 423/161 |
| 8,377,408 | B2 | * | 2/2013 | Dickinson, III ....... | B82Y 30/00 |
| | | | | | 423/445 B |
| 8,420,042 | B2 | * | 4/2013 | Dickinson ............ | B82Y 30/00 |
| | | | | | 423/445 B |
| 8,679,444 | B2 | * | 3/2014 | Noyes .................. | B82Y 30/00 |
| | | | | | 423/447.2 |

OTHER PUBLICATIONS

International Search Report and Written Opinion dated Sep. 10, 2015 from relation International Application No. PCT/US2015/029699.
Olivares-Ramirez J. M. et al.; "Hydrogen Generation by Treatment of Aluminium Metal with Aqueous Solutions Procedures and Uses" INTECH, Chapter 3, 2012.

* cited by examiner

*Primary Examiner* — Stuart L Hendrickson
(74) *Attorney, Agent, or Firm* — Olive Law Group, PLLC

(57) ABSTRACT

In a method for capturing carbon, sulfur, and/or nitrogen from a target source, a matrix including activated metal dispersed in a metal activating agent is provided. The target source may be or include a carbon, sulfur, and/or nitrogen target compound. The target source is contacted with the matrix, wherein the activated metal reacts with the target source to produce elemental carbon, elemental sulfur, elemental nitrogen, and/or one or more compounds transformed from the target compound(s). The matrix may be produced by contacting a metal with the metal activating agent, and maintaining contact between the metal and the metal activating agent for a period of time sufficient for metal atoms from the solid metal to disperse in the metal activating agent. The reaction may also produce a metal compound. The activated metal may also be utilized in alkylation and other synthesis processes.

36 Claims, 17 Drawing Sheets

ACTIVATED METAL LOW TEMPERATURE REACTION PROCESSES AND PRODUCTS

RELATED APPLICATIONS

This application is the national stage of International Application No. PCT/US2015/029699, filed May 7, 2015, titled "ACTIVATED METAL LOW TEMPERATURE REACTION PROCESSES AND PRODUCTS", which claims priority of U.S. Provisional Patent Application Ser. No. 61/991,942, filed on May 12, 2014, titled LOW TEMPERATURE CAPTURE OF CARBON, SULFUR, AND NITROGEN, the contents of both of which are incorporated by reference herein in their entireties.

TECHNICAL FIELD

The present invention relates generally to reactions involving the use of an activated metal such as aluminum and others, and to products produced by such reactions. The invention also relates to methods for activating the metal with the use of a metal activating agent. The invention further relates to processes utilizing the activated metal for capturing carbon, sulfur, and/or nitrogen, or other elemental materials, from carbon, sulfur, and/or nitrogen compounds, respectively, and for transforming such compounds to modify the compounds or produce other compounds. The invention further relates to alkylation processes utilizing the activated metal.

BACKGROUND

Aluminum and certain other metals have high energy content (aluminum being one of the highest) and therefore can be extremely active materials, limited only by surface passivation. The reactivity of aluminum and other metals may be visualized by the well-known Ellingham diagram, which plots the change in Gibbs free energy ($\Delta G$) as a function of temperature for oxidation reactions involving different metals. The driving force for reaction is governed by the bond energy difference with oxide, sulfide, nitride, or phosphide compounds. The Ellingham diagram demonstrates that in addition to aluminum, magnesium, calcium, lithium, and other electropositive species follow this trend. However, such metals are not generally considered as catalysts, reagents, electrophiles, or the like, due to their normal confinement by a passivating oxide that blocks their reactivity potential. Such metals, in order to be active and to continue to remain active after reacting with a target material, need to be in an atomic state unhindered by a passivating oxide. An ongoing need exists for finding ways to exploit the active property of such metals in the context of various chemical and industrial processes, and to renew such metals so that they remain available as an active agent in such processes.

For example, there have been numerous studies relating to removing or capturing transforming carbon dioxide ($CO_2$) from the exhaust of various processes, such as from flue gases from combustion processes, byproducts of fermentation, and byproducts of processes of extraction from the environment. Also of interest is removing pollutants such as $NO_x$ compounds (nitric oxide and nitrogen dioxide), $SO_x$ compounds (sulfur dioxide, sulfur trioxide, etc.), and other sulfur-containing compounds such as carbon disulfide ($CS_2$), carbonyl sulfide (COS), and thiophene ($C_4H_4S$) and the like. These studies have also extended to the removal of carbon compounds, sulfur compounds, nitrogen compounds and other pollutants from synthesized or extracted products such as organic fuels, natural gas, and syngas. Carbon and sulfur capture approaches currently in practice have focused on removal of $CO_2$ and hydrogen sulfide ($H_2S$) from process streams via adsorption in an amine system, with elemental sulfur subsequently isolated via the well-known Claus process. However, these processes require high temperatures and pressures and the use of expensive catalysts to obtain conversion yields on the order of 50% to 70%. Moreover, the amine-based processes are not effective for removing mercaptans, thiophenes, and certain sulfides such as carbonyl sulfide (COS).

Another example is the class of alkylation processes, which utilize an alkylating agent to transfer an alkyl group from one molecule to another. One specific example is the alkylation of isobutane with olefins in oil refining processes. Known nucleophilic alkylating reagents include organometallic compounds such as organomagnesium (Grignard reagents), organolithium, organocopper, and organosodium. Known electrophilic alkylating reagents include those utilized in Friedel-Crafts reactions, using alkyl halides to alkylate aromatic substrates in the presence of a Lewis acid catalyst.

It would be desirable to be able to capture or extract useful materials from the products resulting from chemical and industrial processes, such as elemental carbon from carbon compounds, elemental sulfur from sulfur compounds, and elemental nitrogen from nitrogen compounds. Further, it would be desirable to capture elemental carbon, sulfur, and/or nitrogen by using activated metal as an agent for such capture. Further, it would be desirable to capture such materials without requiring the expense and complexity of heat addition and pressurization, or the use of expensive catalysts although these may be added within ranges that are economical. Further, it would be desirable to implement alkylation processes with the use of activated metal as an agent or catalyst. Further, it would be desirable to utilize the activated metal to simultaneously produce hydrogen locally and at low temperature to facilitate alkylation and other hydration reactions.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one embodiment, a method for capturing a target element from a target source includes: providing a matrix comprising an activated metal dispersed in a metal activating agent; and contacting the target source with the matrix, wherein: the target element is selected from the group consisting of carbon, sulfur, nitrogen, and a combination of two or more of the foregoing; the target source comprises a compound selected from the group consisting of a target carbon compound, a target sulfur compound, a target nitrogen compound, and a combination of two or more of the foregoing; and the activated metal reacts with the target source to produce a product selected from the group consisting of elemental carbon, elemental sulfur, elemental nitrogen, a transformed carbon compound transformed from the target carbon compound, a transformed sulfur compound transformed from the target sulfur compound, a transformed nitrogen compound transformed from the target nitrogen compound, and a combination of two or more of the foregoing.

In some embodiments in which the activated metal reacts with the target source to produce a transformed compound or compounds (e.g., a transformed carbon compound, transformed sulfur compound, and/or transformed nitrogen compound), the method further comprises: producing or liberating the target element (e.g., elemental carbon, elemental sulfur, and/or elemental nitrogen) from the transformed compound(s). In some embodiments, the activated metal may be reacted with the transformed compound(s) to produce or liberate the target element from the transformed compound(s).

According to another embodiment, a method for capturing a target element from a target source includes: providing a matrix comprising activated metal dispersed in a metal activating agent; and contacting the target source with the matrix, wherein: the target element is selected from the group consisting of carbon, sulfur, nitrogen, and a combination of two or more of the foregoing; the target source is selected from the group consisting of a carbon compound, a sulfur compound, a nitrogen compound, and a combination of two or more of the foregoing; and the activated metal reacts with the target source to produce at least one of liberated carbon, liberated sulfur, and liberated nitrogen thereby cleansing the fluid of the targeted materials.

According to another embodiment, a method for capturing a target element from a target source includes: producing a matrix comprising activated metal by contacting solid metal with an metal activating agent, and maintaining contact between the solid metal and the metal activating agent for a period of time sufficient for metal atoms from the solid metal to disperse in the metal activating agent; and flowing the target source into contact with the matrix, wherein: the target element is selected from the group consisting of carbon, sulfur, nitrogen, and a combination of two or more of the foregoing; the target source is selected from the group consisting of a carbon compound, a sulfur compound, a nitrogen compound, and a combination of two or more of the foregoing; and the activated metal reacts with the target source to produce at least one of liberated carbon, liberated sulfur, and liberated nitrogen.

According to another embodiment, the activated metal comprises aluminum (Al), magnesium (Mg), calcium (Ca), barium (Ba), lithium (Li), beryllium (Be), silicon (Si), an alloy of one or more of the foregoing, or a combination of two or more of the foregoing.

According to another embodiment, the metal activating agent comprises gallium, indium, tin, zinc, or a combination of two of more of the foregoing.

According to another embodiment, flowing the target source into contact with the matrix is done at a process temperature in a range from 7° C. to 400° C.

According to another embodiment, flowing the target source into contact with the matrix is done at about room temperature, at about atmospheric pressure, or at both of the foregoing.

According to another embodiment, the reaction produces a metal compound such as, for example, a metal oxide, metal hydroxide, metal carbide, metal sulfide, or metal nitride.

According to another embodiment, the target source is a liquid, a gas, a supercritical fluid, a solid, or a solid dispersion phase.

According to another embodiment, the target source comprises carbon dioxide, sulfur dioxide, sulfur trioxide, carbon disulfide, hydrogen sulfide, thiofuran, thiophenes, mercaptans, ammonia, nitric oxide, nitrogen dioxide, or a combination of two or more of the foregoing.

According to another embodiment, the target source comprises a thiofuran, or a mixture of a thiofuran and one or more of a hydrocarbon, and an alcohol.

According to another embodiment, the target source comprises a hydrocarbon, or a mixture of a hydrocarbon and one or more of water, a hydrated compound, an alcohol, and a compound including a hydroxyl functional group (—OH).

According to another embodiment, flowing the target source into contact with the matrix is done in the presence of a hydrogen source, and while the activated metal reacts with the target source, and the method further comprises generating hydrogen gas, generating a hydrogen compound, or generating both hydrogen gas and a hydrogen compound.

In some embodiments, the hydrogen source is water, alcohol, or both water and alcohol.

According to another embodiment, the target source includes a carbon compound, and flowing the target source into contact with the matrix is done in the presence of a hydrogen source.

The method further includes producing an organic compound such as a hydrocarbon.

According to another embodiment, an organic compound is provided. The organic compound is produced according to any of the methods disclosed herein. In some embodiments, the organic compound is a hydrocarbon.

According to another embodiment, a method for generating electricity includes:

performing a reduction reaction between activated metal and a compound; and channeling the charge transfer associated with the reduction reaction into electrical current.

According to another embodiment, a metal compound is provided. The metal compound is produced according to any of the methods disclosed herein.

According to another embodiment, elemental carbon, sulfur, nitrogen, or a combination of two of more of the foregoing is provided. The elemental carbon, sulfur, nitrogen, or combination is produced according to any of the methods disclosed herein.

According to another embodiment, a system for capturing a target element from a target source is provided. The system may be configured to perform any of the methods disclosed herein.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION

Figure 1:
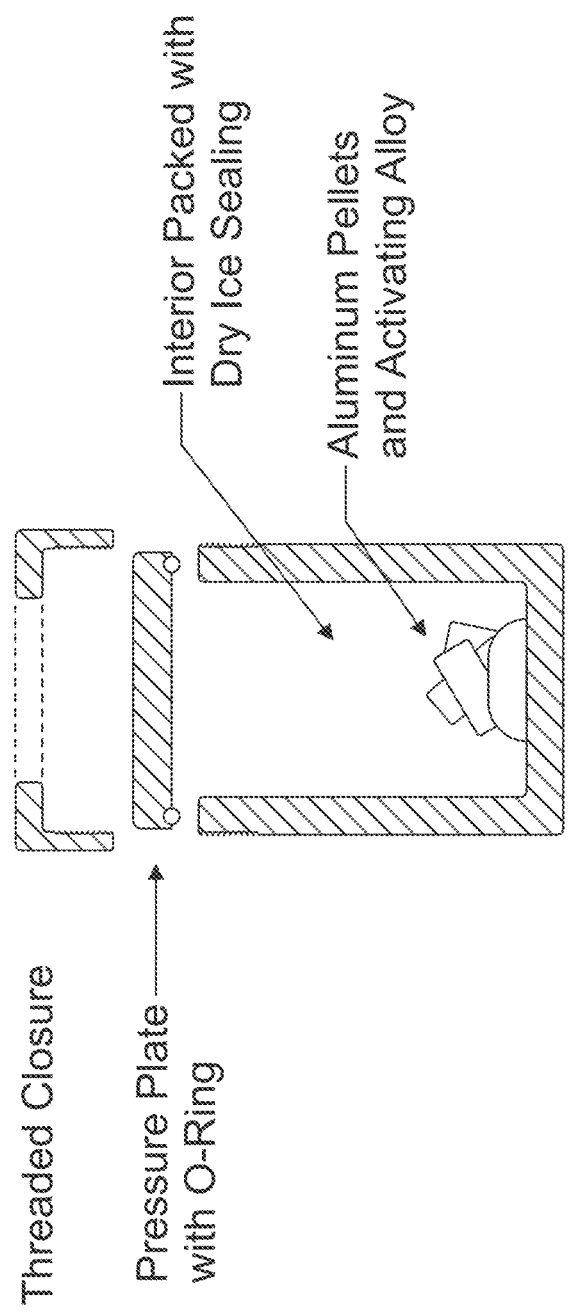
FIG. 1 is a schematic view of a pressure vessel utilized in an experiment conducted in accordance with an embodiment disclosed herein.

The present disclosure describes methods for capturing (or liberating, removing, or producing) a target element from a target source. In some embodiments, the target element is carbon, sulfur, and/or nitrogen. Generally, the target source may be or include any carbon compound, sulfur compound, and/or nitrogen compound. The target compound (e.g., carbon compound, sulfur compound, nitrogen compound) may be one from which elemental carbon, sulfur, or nitrogen may be liberated in accordance with the methods disclosed herein. Examples of carbon compounds, sulfur compounds, or nitrogen compounds include, but are not limited to, carbon dioxide ($CO_2$), sulfur dioxide ($SO_2$), sulfur trioxide ($SO_3$), carbon disulfide ($CS_2$), carbonyl sulfide (COS), thiophene ($C_4H_4S$) and other cyclic compounds, mercaptans (thiols, e.g., methanethiol ($CH_3SH$) and ethanethiol ($C_2H_5SH$)), other organosulfur compounds, hydrogen sulfide ($H_2S$), ammonia ($NH_3$), nitric oxide (NO), and nitrogen dioxide ($NO_2$).

In the context of the present disclosure, unless specified otherwise or the context dictates otherwise, the process of capturing a target element from a target source encompasses capturing the target element itself from a target compound containing the target element, or transforming the target compound to a transformed compound different from the target compound. One example of a transformed compound is a modified form of the target compound in which the molecular structure of the target compound has been altered. For example, a cyclic compound such as thiophene may be modified by a reaction with activated metal as disclosed herein such that the molecular ring is broken. Another example of a transformed compound is a compound having a molecular content different from the target compound but containing the target element that was originally part of that target compound. As an example of the latter, in a case where the target compound is hydrogen sulfide, the transformed sulfur compound may be a different type of sulfur compound where the hydrogen sulfide molecule served as the sulfur source in forming the transformed sulfur compound.

In some embodiments involving transforming the target compound to a transformed compound different from the target compound, the method may further include capturing the target element from the transformed compound. Transforming the target compound may facilitate such capture. Generally, any suitable process may be utilized to produce the target element from the transformed compound. In some embodiments, the activated metal disclosed herein may react with the transformed compound to produce the target element.

The target source may be a liquid, a gas (or vapor), a supercritical fluid, a solid, or a solid dispersion phase. The target source may be, or be a component of, an end product, byproduct, or intermediate product (e.g., an exhaust gas, stream, effluent, etc.) of any chemical or industrial process. Examples of such processes include, but are not limited to, products of combustion (e.g., flue gas), products of fermentation, products of biodegradation, products of ammonia synthesis, products of organic (hydrocarbon) fuel synthesis (e.g., gasoline, diesel, jet fuel, etc.) or other hydrocarbon synthesis, products of syngas synthesis, and products of natural gas extraction. The target source may also be a liquid or a gas naturally present in the environment in which the method disclosed herein is implemented, a few non-limiting examples being ambient air and exhaled breath. Alternatively, the target source may be a liquid or a gas collected and/or prepared (e.g., enriched, concentrated, purified, etc.) specifically for the purpose of implementing the method disclosed herein. The target source may be a compound considered to be predominantly a waste material, pollutant, or toxin, or may have alternative utility if recovered for a purpose such as chemical synthesis, heat or power generation, etc. The target source may be part of a mixture of other materials (e.g., exhaust gas). Depending on the type of other materials, the target source may or may not need to be isolated from such other materials in preparation of performing the method disclosed herein.

In some embodiments, the target source may be a combination of two or more different types of carbon compounds, sulfur compounds, and/or nitrogen compounds, for example a mixture of $CO_2$, $SO_x$, $NO_x$, carbon disulfide ($CS_2$), carbonyl sulfide (COS), and/or thiophene ($C_4H_4S$). In such embodiments, the method disclosed herein may be performed to capture more than one type of target element (i.e., carbon, sulfur, and/or nitrogen), by carrying out either a single iteration of the method or multiple (parallel or serial) iterations.

In some embodiments, the method utilizes an activated metal M* to react with the target source to capture the target element from the target source (i.e., from a compound of the target source containing the target element). In the present context, the asterisk "*" indicates that a metal M is in the activated state. In addition to the captured target element and/or transformed target compound, the reaction may produce at least one compound of the general form MX, where M is the metal that was activated for use in reacting with the target source, and X is an element from the target source or from the environment in which reaction with the activated metal M* occurred. In the present context, "activated" metal refers to a metal that has been rendered in a form that is exceptionally receptive to chemical reaction, as taught herein. Metals that may be activated, and which in the activated state are effective for capturing a target element (or transforming a target compound), in accordance with the present disclosure include, but are not limited to, aluminum (Al), magnesium (Mg), calcium (Ca), barium (Ba), lithium (Li), beryllium (Be), and silicon (Si). An activated metal may be effective for capturing a target element while existing in an alloy. For example, an Al/Mg has been found to be able to be activated in the manner disclosed herein.

According to the method, a matrix including activated metal M* dispersed (or "dissolved") in a suitable metal activating agent is provided. The metal activating agent may be a liquid or other flowable material, or may be a solid. If a solid, the metal activating agent may, at least initially, be soft and malleable, although may become brittle as a result of implementation of the method. The metal activating agent may include one or more metals. At least one of the metals comprising the metal activating agent is a metal species effective for activating a metal reactant M in the manner described herein. The metal activating agent may be a single-component material or may be an alloy (e.g., binary, ternary, quaternary, etc.). Examples of suitable metal activating agents include, but are not limited to, gallium, indium, tin, zinc, and combinations of two or more of the foregoing. In one specific yet non-limiting example, the metal activating agent is a gallium/indium/tin alloy. The metal activating agent may be a eutectic material (typically, a eutectic alloy). In some embodiments, only a small amount of activated metal M* is needed for the successful implementation of the method. For example, the concentration of the activated metal M* in the matrix may be as low as about <0.01%. The maximum concentration of the activated metal M* in the matrix is limited by the type of metal activating agent utilized and the techniques now known or later developed for forming a dispersion of the activated metal M* in the metal activating agent. For example, in the case of Al* being the activated metal M*, the concentration of the aluminum in a gallium/indium/tin eutectic alloy may be as high as about 50%. Thus, in some embodiments, the concentration of aluminum in the matrix may be in a range from less than 0.01% to 50%.

The activated metal M* in the matrix metal alloy system may react with materials that have lower bond energies such as $H_2O$, $CO_2$, $SO_x$, $H_2S$, NOR, $CS_2$, COS, and $C_4H_4S$. The heat of formation for $CO_2$ is greater than that of $H_2O$. Therefore, there is a greater tendency for the activated metal M* to react with $CO_2$ than with $H_2O$. In the presence or two or more target materials with different affinities for the activated species, the activated species may capture or transform both target materials in accordance with the ratio of the two or more target materials and the ability they have to reach the activated species.

In some embodiments, the matrix is provided with the activated metal already dispersed in the metal activating agent to a desired concentration, i.e., the matrix has already been prepared. In other embodiments, the method includes producing the activated metal by contacting the solid metal reactant (e.g., Al, Mg, Ca, etc. as noted above) with the metal activating agent, and maintaining contact between the solid metal reactant and the metal activating agent for a period of time sufficient for atoms from the solid metal reactant to disperse in the metal activating agent. The solid metal reactant (or an alloy thereof) may be provided in any suitable form, for example, a rod (or wire), a plate, a container (bowl, dish, can, etc.), a pellet (or bead), a powder (or granules), etc. Generally, no limitation is placed on the purity of the solid metal reactant utilized, although higher purity metal reactant may result in more rapid and/or higher yields of the target element to be captured or the target compound to be transformed. It is presently contemplated that the purity levels of solid metal reactants such as aluminum commercially available are sufficient for implementing the method. Generally, no limitation is placed on the particular mechanism by which the atoms of the solid metal reactant become dispersed in the metal activating agent, so long as the resulting matrix is available for exposure to the target source for reaction with the activated metal. Atoms from the solid metal reactant may diffuse or migrate into the metal activating agent, and/or the metal activating agent may diffuse or migrate into the solid metal reactant. The metal activating agent may diffuse along the outer surface of the solid metal reactant and/or grain boundaries, creating activated metal along the way.

According to the method, the target source and the matrix are brought into contact with each other such as, for example, by flowing the target source into contact with the matrix. Thereafter, the activated metal reacts with the target source to capture carbon, sulfur, and/or nitrogen (producing elemental carbon, sulfur, and/or nitrogen, and/or a transformed compound containing carbon, sulfur, and/or nitrogen), depending on the target source. As noted elsewhere in this disclosure, the reaction may also produce a metal compound. The reaction is effective over a wide range of operating conditions. In some embodiments, the process temperature at which the target source contacts the matrix (and at which the reaction occurs) is in a range from about 7° C. to about 400° C. The process pressure may range from sub-atmospheric pressure to above atmospheric pressure. In particular, the method may be successfully carried out under (at or near) ambient conditions, i.e., standard temperature and pressure (room temperature and atmospheric pressure). That is, heat addition and pressurization, and their attendant costs, are not required. It is presently believed that prior to the invention disclosed herein there has not existed a means for capturing target elements such as carbon (or transforming target compounds), or alkalation processes with hydrogen generated local to the reactant, at or near room temperature and/or at about atmospheric pressure.

During the course of the method, or in subsequent iterations of the method, the matrix may be replenished or rejuvenated with fresh (unreacted) metal reactant as needed to replenish the amount of activated metal available for reaction with the target source. The metal activating agent may also be periodically replaced, but generally it has been found that only a negligible amount of metal activating agent material is consumed during the course of the method. That is, the metal activating agent utilized according to the method disclosed herein may be characterized as being substantially inert to the activated metal, the target source, and products of the reaction between the activated metal and the target source.

Prior to contact with the target source, the matrix may be placed or formed on a substrate. In some embodiments the substrate may have the same composition of the metal reactant (e.g., aluminum in embodiments utilizing Al*), thereby providing an additional source of the metal reactant and/or helping to avoid contamination of the matrix. In some embodiments, the substrate may be a container. In some embodiments, the container may be an open container. In this case, the target source may be flowed through the opening and into contact with the matrix contained in the container. An open container may be utilized in either a batch or continuous embodiment of the method. For example, the target source if in liquid form may be dispensed into the container, and the reaction with activated metal allowed to proceed until a desired amount of the target element has been captured. As another example, a flow of the target source if in gaseous form may be directed into the container, and the flow continued until a desired amount of the target element has been captured. In other embodiments, the container may be a closed container. The closed container may or may not be pressurized, and may or may not be sealed from the ambient in a fluid-tight manner. A closed container may likewise be utilized in either a batch or continuous embodiment of the method. For example, in a batch process, the closed container may include a single opening that is closed (e.g., using a lid or a valve) after being loaded with a desired amount of the target source. As another example, in a continuous process, the closed container may include an inlet for introducing the target source into the interior, and an outlet for collecting the unreacted fraction of the target source and any liberated target element material entrained in the unreacted fraction.

In some embodiments, the substrate may be configured to present a large-area surface for supporting the matrix, thereby providing a large surface area of the matrix available for exposure to the target source. In the case of a container, for example, the container may have a relatively large bottom inside surface (relative to the height of the container) on which the matrix resides. As another example, the substrate may have a cylindrical configuration. In this case, the matrix may be applied as a coating (or layer) on the cylindrical substrate. Alternatively, the matrix may be formed on the cylindrical substrate by providing (e.g., depositing according to any suitable technique as appreciated by persons skilled in the art) the metal reactant (e.g., a solid metal) as a coating (or layer) on the cylindrical substrate and applying the metal activating agent as a coating (or layer) on the metal reactant, or by applying the metal activating agent directly to the cylindrical substrate and subsequently providing a coating of the metal reactant on the metal activating agent. Alternatively, the metal reactant may be provided in a cylindrical form (e.g., a rod or wire) and thus serve as the substrate. In this case, the metal activating agent may be applied to the cylindrical metal reactant structure, whereby a matrix containing a dispersion of activated metal at a desired concentration is produced after a sufficient period of time. It will be understood that a cylinder is just one example of a shape for the substrate or solid metal reactant, and that other shapes that increase the surface area available for interaction with the target source may alternatively be utilized.

As noted above, in some embodiments a metal compound MX is produced. The type of metal compound MX produced will depend upon the particular embodiment being implemented. Examples include, but are not limited to, metal oxide, metal hydroxide, metal carbide, metal sulfide, and metal nitride. In some embodiments, the method includes recovering the metal reactant from the metal compound. The recovered metal reactant may be utilized as a source of activated metal, such as for replenishing the matrix as described above. The metal reactant may be recovered by subjecting the metal compound to any reduction reaction suitable for its composition, as appreciated by persons skilled in the art.

In some embodiments, the method includes contacting the target source with the matrix in the presence of a hydrogen source, for example, water and/or an alcohol (e.g., ethanol). Such embodiments may result in the synthesis of a hydrocarbon compound in addition to a metal compound and a liberated target element. In some cases the reaction can take place between two or more organic molecules producing new desired products. Such embodiments may also result in the localized generation of hydrogen gas, which may be useful in synthesizing organic compounds or facilitating other reactions.

In some embodiments, the method includes contacting the target source with the matrix in the presence of a nitrogen source, for example, ammonia. Such embodiments may result in the synthesis of a metal nitride compound of high value (e.g., AlN, $Si_xN_y$, etc.) in addition to a liberated target element. For example, high-purity AlN is desirable for its high dielectric constant and high thermal conductivity. It may be possible to grow single crystals of the metal nitride compound out of the activated matrix at low temperatures. Moreover, such embodiments may produce pure hydrogen and/or nitrogen as a byproduct. Depending on activated metal utilized, other metal nitrides may also be formed, as well as metal oxides. Thus, in some embodiments, the method may be utilized in the production of ceramics.

Experiments conducted thus far have demonstrated the capture of carbon from carbon dioxide, sulfur from sulfur dioxide, carbon and sulfur from carbon disulfide, and nitrogen from ammonia. Some Examples are set forth below. Thus, the method may be implemented in the purification or "clean up" of output streams containing carbon compounds, sulfur compounds, and/or nitrogen compounds, such as syngas, natural gas, organic fuel, etc. The method is capable of removing impurities from both "sour" (high impurity content) and "sweet" (low impurity content) output streams. Depending on the application, the method may be implemented as a upstream or downstream addition to an existing clean-up process, such as the various known acid gas removal (AGR) processes utilizing proprietary solvent or sorbent formulations (or in some cases membranes), or may serve as a more economical (low-temperature, low-pressure) substitute for existing clean-up processes. The matrix material disclosed herein is essentially fully renewable, similar to the regeneration of solvents, sorbents, and catalysts.

It is further contemplated that the method may be effective for preferentially removing more complex compounds such as certain undesired aromatic compounds from output streams. For example, the method may be effective for preferentially transforming thiophene (or thiofuran, a heterocyclic compound with the formula $C_4H_4S$), thiophene compounds, and derivatives thereof from thiophene-containing hydrocarbons such as, for example, petroleum compounds and higher-grade fuel compounds (e.g., gasoline, diesel, jet fuel, etc.). The method may also be effective for transforming mercaptans (thiols). The method may also be effective for removing sulfur from such compounds.

In additional embodiments, methods for generating electricity are provided. Such methods may utilize a device configured for channeling the electron transfer inherent in reduction reactions involving activated metal through an external circuit. Such methods may be extended to harvesting the energy of reduction involving the reaction of activated metal with a variety of carbon, sulfur, and nitrogen compounds such as, for example, $CO_x$, $SO_x$, and $NO_x$, carbon disulfide ($CS_2$), carbonyl sulfide (COS), thiophene ($C_4H_4S$), mercaptans, and related or derivative compounds. The electrical energy may be stored in a suitable battery.

In further embodiments, the activated metal may be brought into contact with $CO_2$, or both $CO_2$ and $H_2O$, under conditions that result in a violent or even explosive reaction, which may then be utilized to produce mechanical motion, or mechanical motion followed by conversion into electrical energy, or synthesis of compounds. For example, an engine based on a piston and cylinder may be provided, similar to an internal combustion engine. The piston and cylinder may be configured to attain a volumetric compression ratio during the compression stroke similar to that of a gasoline engine, or a comparatively higher compression ratio typical of a diesel engine. In operation, the cylinder is charged with liquid or gaseous $CO_2$ which, during the compression stroke, is raised to the supercritical $CO_2$ state, due to the high compression ratio and thus high pressure achieved. A spray of the activated metal/metal activating agent matrix is then injected into the cylinder and thus into contact with the supercritical $CO_2$, resulting in an intense, high-energy reaction. The reaction may be utilized for various purposes as noted above (mechanical motion, conversion into electrical energy, etc.). As also noted above, the products of the reaction (e.g., liberated carbon, aluminum oxide, etc.) may be collected for further use. In addition to the activated metal/metal activating agent matrix, other reactants may be injected into the cylinder to produce desired products. For example, the addition of water or methane may result in the production of contaminant-free syngas ($H_2$+CO).

Embodiments of the present subject matter also encompass the use of the activated metal as an active agent in alkylation processes, which introduces a broad opportunity for isomerization and olefin synthesis. In the course of the present work, experiments have been performed in hexane, heptane, pure thiophene, and isooctane with thiophene added to ppm levels comparable to commercially-found levels, e.g., 400 ppm. It was observed that activated aluminum (Al*) appears to react with thiophene, and that Al* with the activated matrix M* appears to react more readily in alkane fluids, i.e., the Al rods corrode faster. When the Al rod was removed from the alkane fluid for optical observation for about 10 to 15 minutes, the surface of the Al rod is observed to be continuously erupting with white "tubulars" growing in real time. When the Al rod is placed back into the alkane fluid, bubbles evolved for about 10 minutes. It is postulated that the bubbles were hydrogen from water vapor picked up during the exposure of the Al rod to air. After about 48 hours, the alkane fluid was removed and a wax-like or grease-like residue was observed in the container. It is postulated that this residue is evidence that an alkylation process has taken place.

In another embodiment, one or more hydrogen-generating species such as water and/or alcohol (e.g., ethanol) are added to the hydrocarbon liquid with the activated material in the activating matrix, generating hydrogen that enhances reactions involved in removing sulfur compounds from the hydrocarbon. Experiments conducted by the inventor demonstrate that small additions of water and/or ethanol increase the sulfur reduction process and are effective in attacking the molecular configuration of stable sulfur-containing compounds such as sulfides, thiophenes, and mercaptans. In some experiments, calcium was found to react directly with the water and/or alcohol in the hydrocarbon liquid without the activated matrix.

Example 1

In one example, referring to FIG. 1, solid aluminum and an alloy of gallium/indium/tin (Ga/In/Sn) were placed in a stainless steel container (height=2.5 in, diameter=2.0 in) (specifically, a Spex vial, i.e., a pressure vessel normally utilized for ball milling as appreciated by persons skilled in the art). Dry ice (frozen $CO_2$) was then packed into the container on top of the solid aluminum and Ga/In/Sn alloy. The container was then sealed with a pressure plate, an O-ring positioned between the pressure plate and the open top of the container, and screw-on cap. After a period of time, the dry ice sublimed to gaseous carbon dioxide and the pressure in the container increased to 800 psi. Under this pressure, the carbon dioxide condensed to liquid form. The container was left in this condition overnight, and afterwards was opened. The reacted sample was covered by a black layer, and found to contain amounts of elemental carbon and aluminum oxide ($Al_2O_3$). TABLE 1 below provides atomic concentrations and related data obtained using X-ray photoelectron spectroscopy (XPS) to examine the surface of the sample. The concentration of carbon as determine by the C is region was 23.7 atomic percent, which exceeded the amount of aluminum which was 19.6 percent. The dominant species was oxygen at 52.3%. Minor contributions were observed due to Ga, In, and Sn.

TABLE 1

| Region | Position (eV) | FWHM | Area | Atom % |
| --- | --- | --- | --- | --- |
| C 1s | 285.0 | 2.630 | 3265 | 23.7 |
| O 1s | 532.0 | 3.148 | 21154 | 52.3 |
| Ga 2p3/2 | 1118.5 | 2.759 | 7915 | 2.7 |
| Al 2p | 74.5 | 2.264 | 1457 | 19.6 |
| In 3d | 444.5 | 2.834 | 1655 | 0.5 |
| Sn 3d | 486.5 | 4.520 | 4125 | 1.2 |

TABLE 2 below provides data acquired from an energy-dispersive X-ray spectroscopy (EDS) analysis on the sample taken at an acceleration voltage of 20 kV. The carbonaceous material captured is from about 9.1% to about 10.9% carbon.

TABLE 2

| Chemical formula | ms % | mol % | Sigma | Net | K ratio | Line |
| --- | --- | --- | --- | --- | --- | --- |
| C* | 6.01 | 10.89 | 0.21 | 17345 | 0.0043404 | K |
| O | 48.79 | 66.44 | 0.18 | 527019 | 0.4478670 | K |
| Al | 20.59 | 16.63 | 0.13 | 840897 | 0.2366206 | K |
| Ga | 11.56 | 3.61 | 1.33 | 85896 | 0.2346801 | K |
| In | 5.77 | 1.09 | 0.35 | 162409 | 0.1115407 | L |
| Sn | 7.28 | 1.34 | 0.40 | 184982 | 0.1240980 | L |
| Total | 100.00 | 100.00 | | | | |

TABLE 3 below provides data from an EDS analysis taken at 20 KV on the same sample but in a different spot.

TABLE 3

| Chemical formula | ms % | mol % | Sigma | Net | K ratio | Line |
|---|---|---|---|---|---|---|
| C* | 5.72 | 9.27 | 0.41 | 19158 | 0.0047940 | K |
| O | 56.21 | 68.38 | 0.24 | 1024949 | 0.8710147 | K |
| Al | 27.70 | 19.98 | 0.20 | 1687820 | 0.4749371 | K |
| Ga | 5.71 | 1.59 | 2.37 | 54121 | 0.1478659 | K |
| In | 2.09 | 0.35 | 0.61 | 75795 | 0.0520551 | L |
| Sn | 2.57 | 0.42 | 0.71 | 83961 | 0.0563265 | L |
| Total | 100.00 | 100.00 | | | | |

TABLE 4 below provides data from an EDS analysis taken at 20 KV on a sample from a different experimental run.

TABLE 4

| Chemical formula | ms % | mol % | Sigma | Net | K ratio | Line |
|---|---|---|---|---|---|---|
| C* | 4.53 | 9.11 | 0.41 | 15565 | 0.0038949 | K |
| O | 40.12 | 60.59 | 0.32 | 567987 | 0.4826822 | K |
| Al | 23.72 | 21.24 | 0.23 | 1265607 | 0.3561301 | K |
| Ga | 17.98 | 6.23 | 2.21 | 187016 | 0.5109506 | K |
| In | 6.22 | 1.31 | 0.59 | 238401 | 0.1637311 | L |
| Sn | 7.44 | 1.52 | 0.68 | 258268 | 0.1732631 | L |
| Total | 100.00 | 100.00 | | | | |

Figure 2:
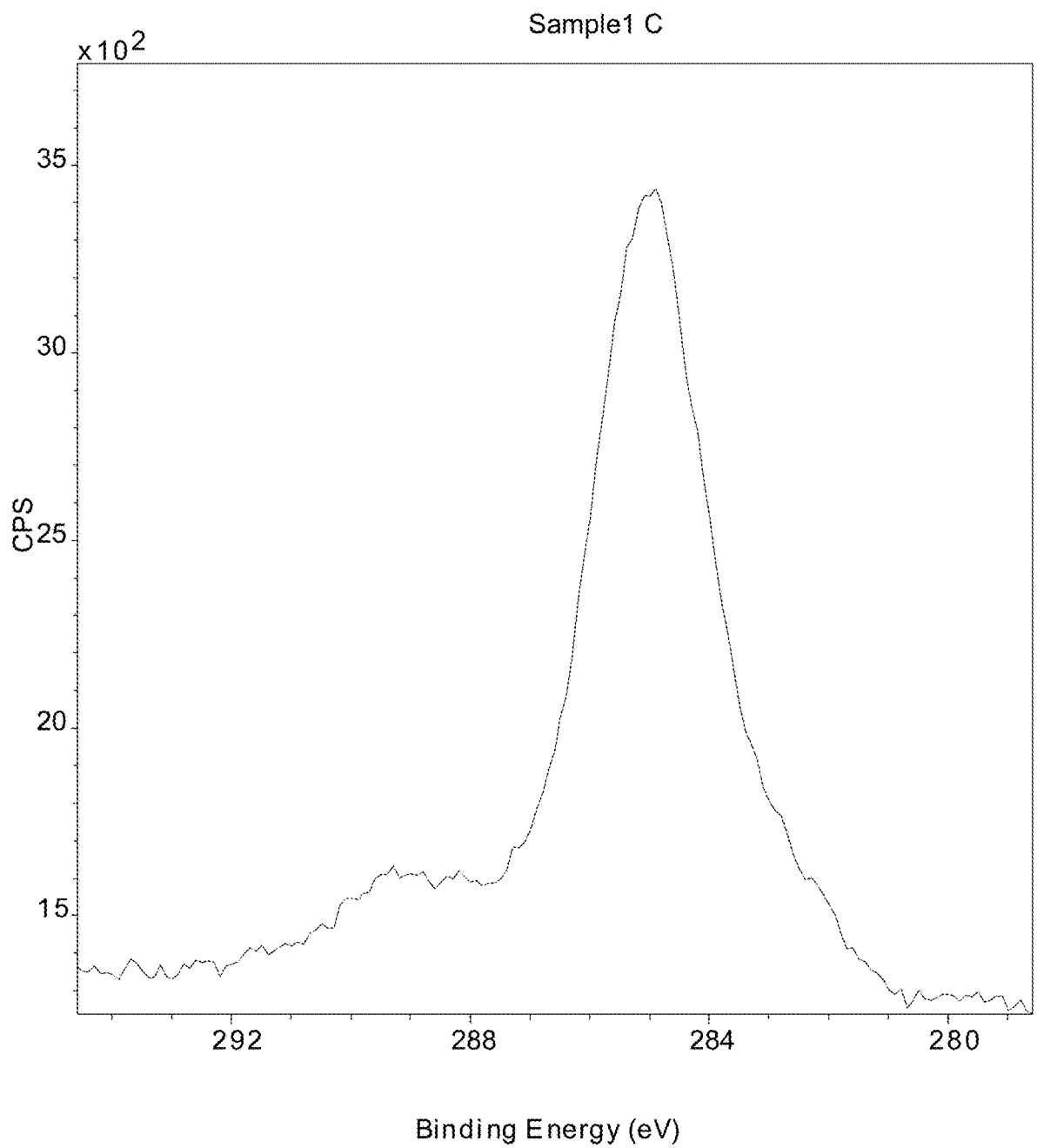
FIG. 2 is a C 1s spectrum obtained using XPS to examine the surface of an aluminum sample combined with alloy and then exposed to $CO_2$ inside a sealed container overnight.

FIG. 2 is a C 1s spectrum obtained using XPS to examine the surface of an aluminum sample combined with alloy and then exposed to $CO_2$ inside a sealed container overnight as described above in conjunction with FIG. 1. The dominant peak at 285 eV in the C is region shown in FIG. 2 is typically due to the presence of carbon bonded to carbon or carbon bonded to hydrogen. Minor contributions were observed at higher binding energies such as 288 and 289 eV, which are typical of oxidized carbon such as alcohols, esters, or carboxyls. Some contribution could be attributed to adventitious carbon, but the high concentrations observed provided evidence that carbon dioxide was reduced to carbonaceous material on the surface of the metal.

Figure 3:
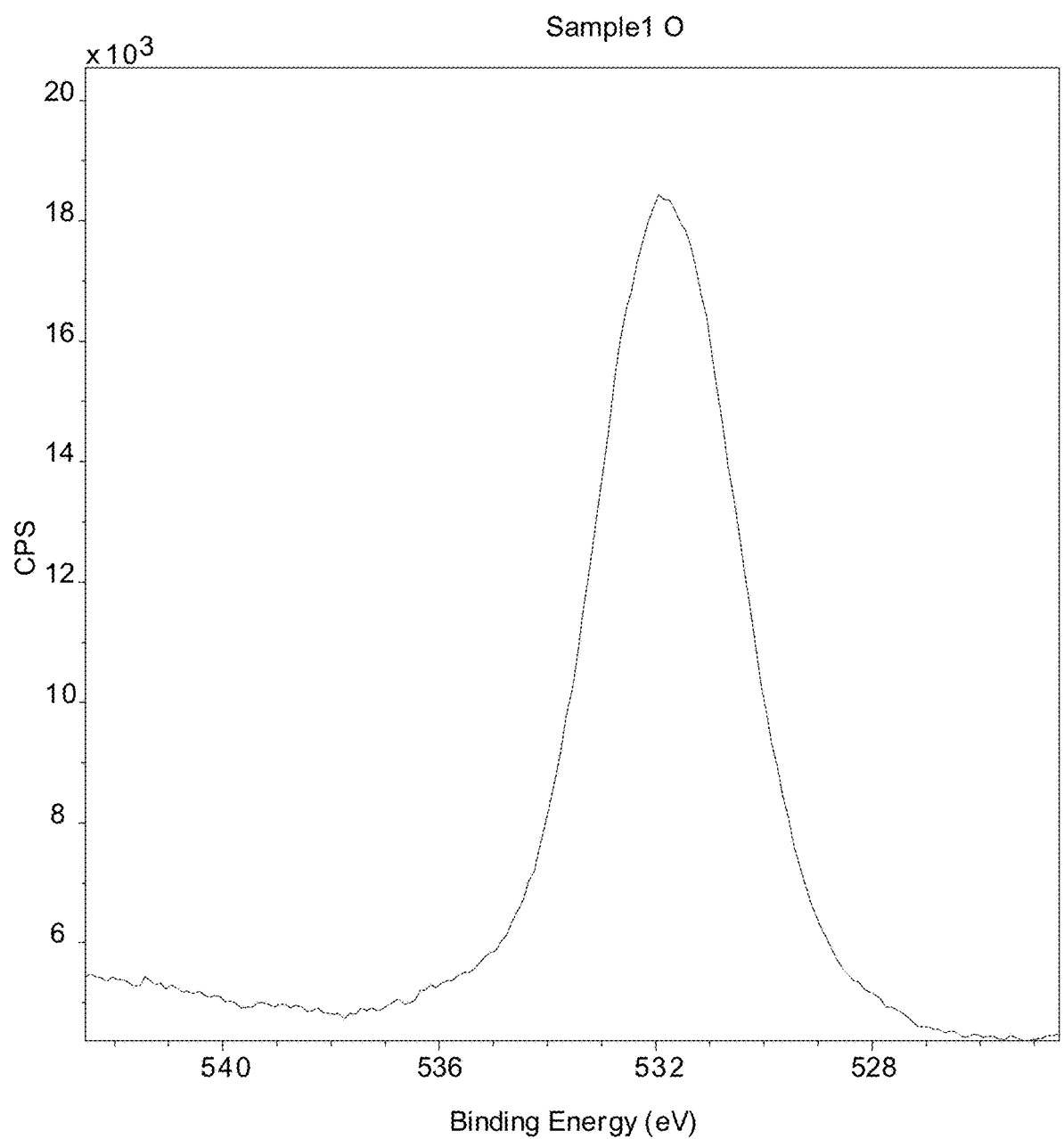
FIG. 3 is an O 1s spectrum using XPS to examine the surface of the same sample as relates to FIG. 2.

FIG. 3 is an O 1s spectrum using XPS to examine the surface of the same sample as relates to FIG. 2. By examining the O 1s region shown in FIG. 3, the dominant peak at 532.0 eV is due to metal oxide rather than oxygen bonded to carbon which would appear at higher binding energies.

Figure 4:
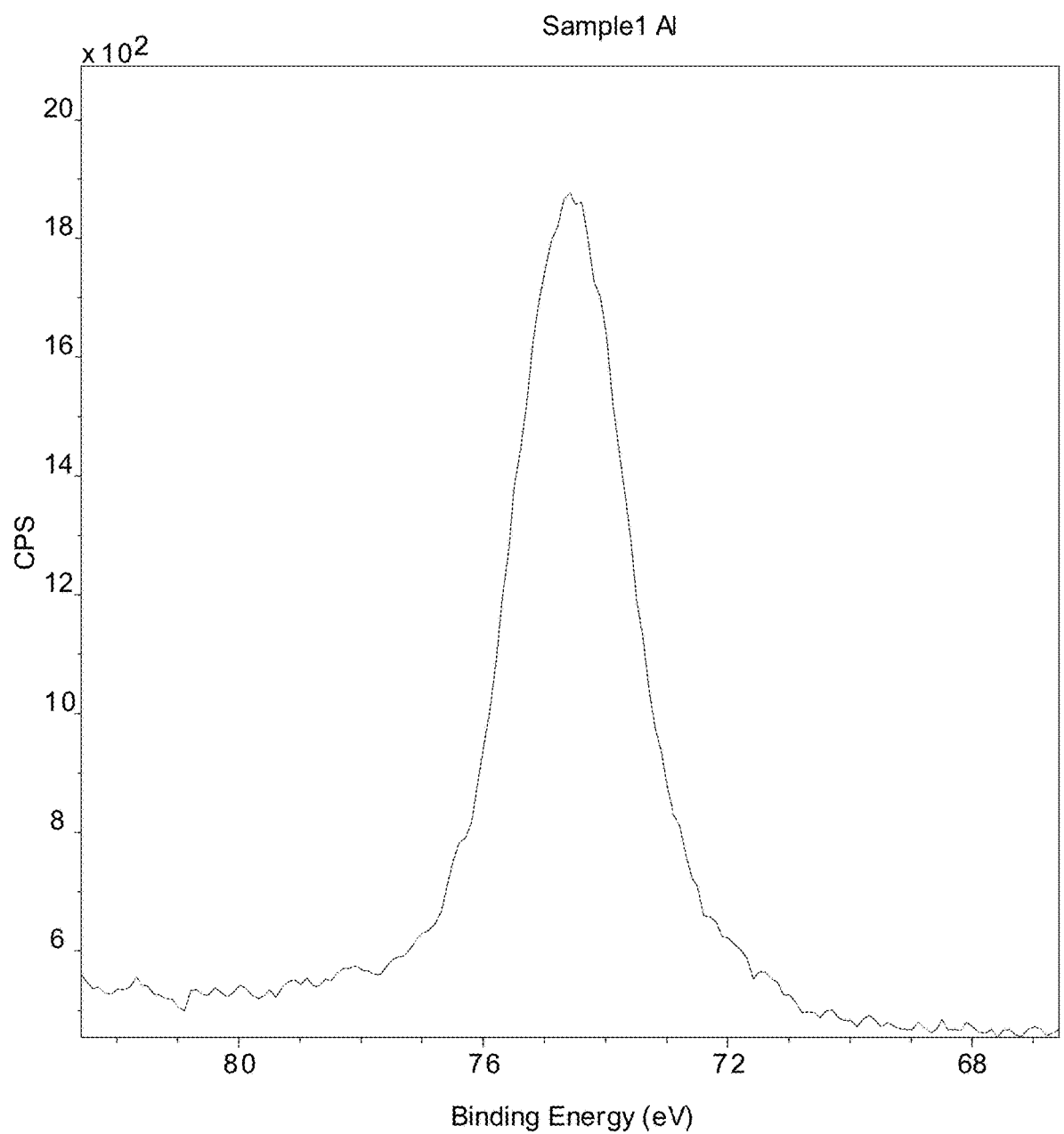
FIG. 4 is an Al 2p spectrum using XPS to examine the surface of the same sample as relates to FIGS. 2 and 3.

FIG. 4 is an Al 2p spectrum using XPS to examine the surface of the same sample as relates to FIGS. 2 and 3. The position of a singe Al 2p peak at 74.5 eV shown in FIG. 4 is also evidence of metal oxide. The absence of metallic aluminum which would appear near 73 eV indicated that all of the aluminum present was in an oxidized form. While there were minor contributions from Ga, In, and Sn, it can be concluded that the dominant oxygen species is aluminum oxide.

Example 2

Figure 5:
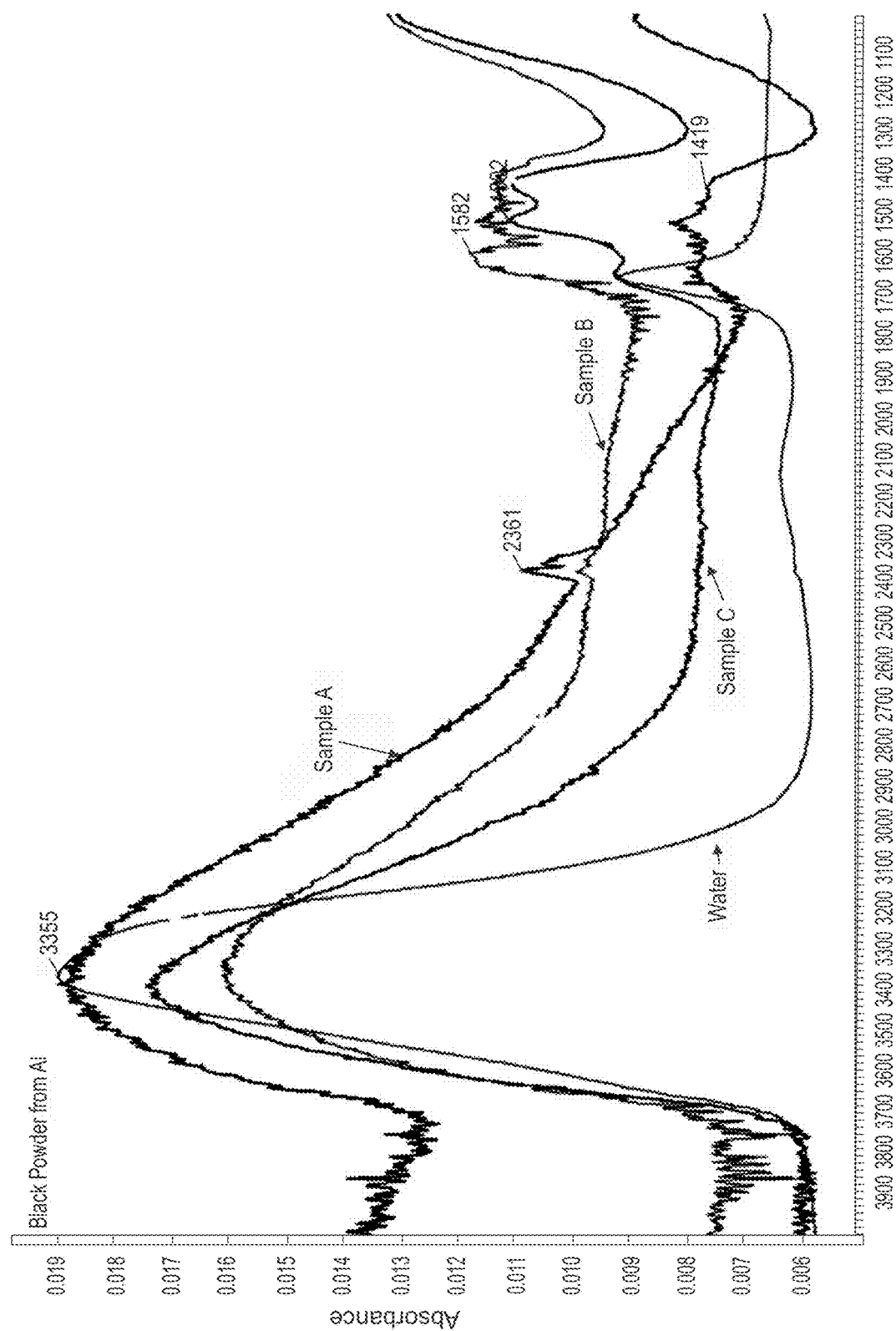
FIG. 5 is a set of ATR FTIR spectra obtained from samples from another experiment.

In another experiment, pure aluminum foil was placed in a petri dish that was inside of a plastic bag (glove bag) containing dry ice and then sealed. The alloy, also inside the bag, was placed onto the aluminum and rubbed lightly in order to disrupt the native oxide. After sitting overnight at ambient conditions, most of the aluminum was covered by a black coating and there were areas of black powder in the petri dish. Water was added to the petri dish and swirled, then allowed to evaporate in an attempt to separate the alloy and aluminum from the reaction products. Three random areas of the black powder were taken, labeled sample A, B, and C, then analyzed using a Fourier Transform Infrared Spectroscopy (FTIR) using a Pike MIRacle ATR accessory equipped with a single reflectance ZnSe crystal. The ATR FTIR spectra obtained from those samples are shown in FIG. 5.

Each of the three random Samples A, B, and C exhibited four rather broad peaks located near 3350, 1580, 1502 and 1419 $cm^{-1}$. The only significant difference was intensity and/or noise, which is likely due to uneven pressure as the sample is placed against the ZnSe crystal. In these samples, since water was added, a reference spectrum was obtained from water which is also shown in FIG. 5. Water exhibits a broad peak near 3350 and second peak near 1600, both related to O—H chemistry. Significant hydrogen bonding is present in all samples as exhibited by the broad peaks.

Figure 6:
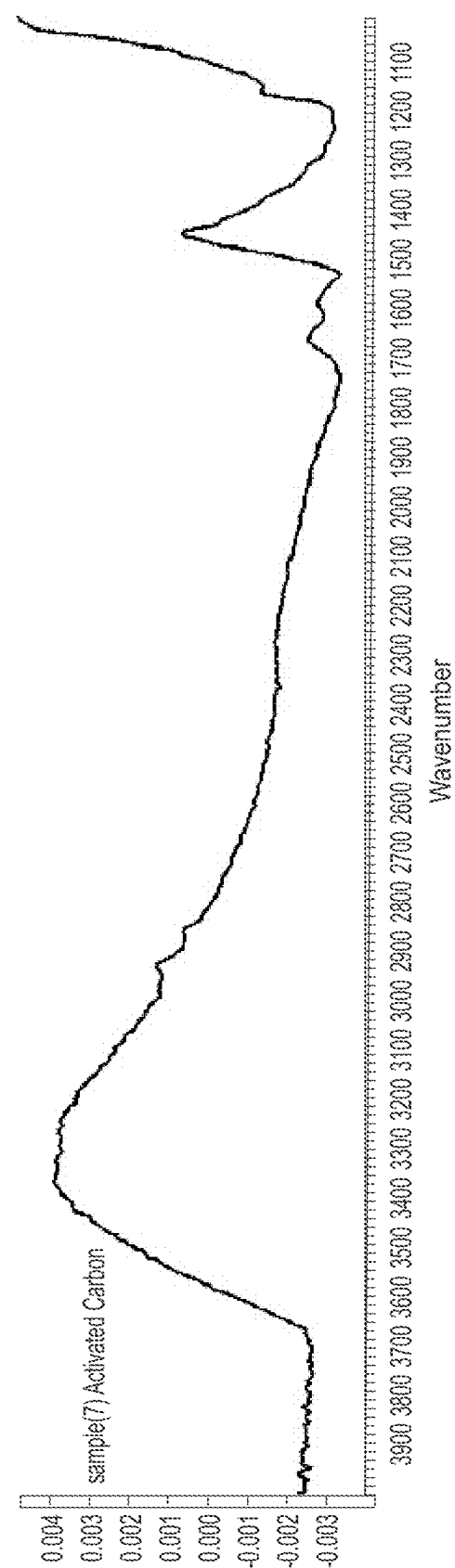
FIG. 6 is an ATR FTIR spectrum obtained from a reference sample as part of the same experiment relating to FIG. 5.

In order to identify the remaining peaks, a reference sample of activated carbon was analyzed in the same manner. The resultant ATR FTIR spectrum shown in FIG. 6, exhibited both similar and dissimilar features. The similar features were observed near 1400 to 1500 $cm^{-1}$, which are typically due to C—C—C type vibrations, often referred to as backbone structure. Carbon black that is activated can be treated with oxygen or acids in order to provide surface functionality to what would otherwise be carbon. These dissimilar features are evident in FIG. 6 by the presence of peaks near 1600 and 1650 $cm^{-1}$ related to carbonyl vibrations, and the broad peak near 3350 due to O—H vibration, which could be either due to water or from acidic functionality or both. The activated carbon sample also showed peaks near 2850 to 2950 $cm^{-1}$ due to $CH_2$ and $CH_3$ hydrocarbons. It will be noted that peaks near 2360 $cm^{-1}$ are due to $CO_2$ from air not completely purged from the instrument during analysis.

Example 3

Figure 7:
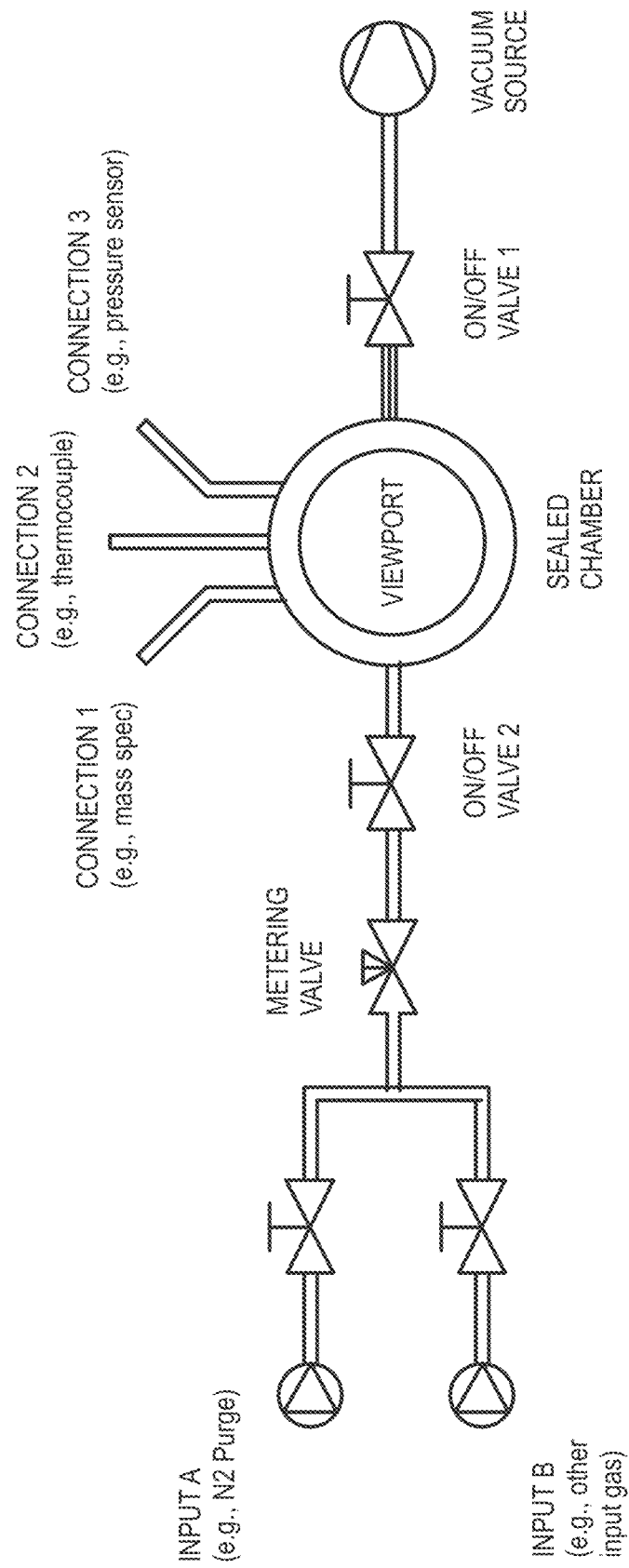
FIG. 7 is a schematic view of a sealed chamber and associated system utilized in an experiment conducted in accordance with an embodiment disclosed herein.

In another example, an aluminum container was formed by machining a dimple into a block of aluminum (about 1 $cm^2 \times 0.25$ cm). The dimple was filled with an alloy of gallium/indium/tin. An aluminum slug was inserted through the Ga/In/Sn alloy into contact with the surface of the aluminum block and rubbed against this surface, thereby removing the oxide film (and hence de-passivating the aluminum surface) directly under the Ga/In/Sn alloy. The container was then placed in a sealed chamber. The chamber was initially evacuated and then filled with carbon dioxide gas to a pressure above atmospheric pressure. The reaction was allowed to proceed at room temperature. FIG. 7 is a schematic view of the chamber and associated system. As shown, the chamber includes a viewport and appropriate connections were made to measuring and sensing instruments (mass spectrometer, thermocouple, pressure sensor), as appreciated by persons skilled in the art. The inlet side of the system included sources for nitrogen purge gas and other gases followed by respective on/off valves. A common input line from the gas feeds was regulated by a metering valve and an on/off valve. The outlet side of the system included an on/off valve and vacuum source.

Quantitative measurement demonstrated that the pressure decayed to below atmospheric pressure, indicating pumping by the Ga/In/Sn alloy with the active material being the activated aluminum. At the start of the experiment, the aluminum components and the Ga/In/Sn alloy were shiny as expected. Over time, these components turned black as a result of the reaction of the activated aluminum and the carbon dioxide. Data from an EDS analysis of different areas of the surface of the sample are set forth in Tables 5 to 9 below. It will be noted that the compositions at 5 kV are lower in carbon concentration than at 20 kV because at the higher acceleration voltage a larger volume of material is measured. It will also be noted that at the higher voltages the matrix is also shown.

TABLE 5

EDS on edge spot 1 5 kV

| Chemical formula | ms % | mol % | Sigma | Net | K ratio | Line |
|---|---|---|---|---|---|---|
| C | 6.07 | 9.09 | 0.19 | 30110 | 0.0121644 | K |
| N* | 5.53 | 7.1 | 0.55 | 19725 | 0.0631765 | K |
| O | 54.49 | 61.23 | 0.32 | 524978 | 0.623826 | K |
| Al | 33.91 | 22.59 | 0.87 | 293327 | 0.3534125 | K |
| Total | 100.00 | 100.00 | | | | |

TABLE 6

EDS on edge spot 1 20 kV

| Chemical formula | ms % | mol % | Sigma | Net | K ratio | Line |
|---|---|---|---|---|---|---|
| C | 12.54 | 21.47 | 0.13 | 35153 | 0.0087964 | K |
| N* | 4.13 | 6.07 | 0.32 | 10037 | 0.033683 | K |
| O | 42.99 | 55.24 | 0.17 | 302415 | 0.2569958 | K |
| Al | 14.89 | 11.34 | 0.09 | 496206 | 0.1396279 | K |
| Ga | 11.72 | 3.46 | 0.95 | 71673 | 0.1958206 | K |
| In | 7.99 | 1.43 | 0.24 | 188175 | 0.1292362 | L |
| Sn | 5.73 | 0.99 | 0.28 | 121468 | 0.0814889 | L |
| Total | 100.00 | 100.00 | | | | |

TABLE 7

EDS on spot 2 20 kV

| Chemical formula | ms % | mol % | Sigma | Net | K ratio | Line |
|---|---|---|---|---|---|---|
| C | 15.82 | 21.29 | 0.33 | 106746 | 0.0267112 | K |
| O | 68.71 | 69.44 | 0.27 | 1812700 | 1.5404558 | K |
| Al | 15.47 | 9.27 | 0.23 | 1302363 | 0.3664731 | K |
| Total | 100.00 | 100.00 | | | | |

Data from an EDS analysis of an area on the surface of another sample from another experimental run are set forth in Tables 8 and 9 below.

TABLE 8

EDS 5 kV

| Chemical formula | ms % | mol % | Sigma | Net | K ratio | Line |
|---|---|---|---|---|---|---|
| C | 5.98 | 9.21 | 0.21 | 107490 | 0.0263159 | K |
| O | 56.01 | 64.74 | 0.32 | 2109391 | 1.518985 | K |
| Al | 38.01 | 26.05 | 0.92 | 1241576 | 0.90652 | K |
| Total | 100.00 | 100.00 | | | | |

TABLE 9

EDS 20 kV

| Chemical formula | ms % | mol % | Sigma | Net | K ratio | Line |
|---|---|---|---|---|---|---|
| C* | 7.06 | 11.73 | 0.41 | 23181 | 0.0058006 | K |
| O | 49.59 | 61.84 | 0.23 | 912486 | 0.7754422 | K |
| Al | 32.02 | 23.68 | 0.17 | 2158828 | 0.6074745 | K |
| Ga | 7.03 | 2.01 | 2.09 | 73051 | 0.1995841 | K |
| In | 2.58 | 0.45 | 0.55 | 101398 | 0.0696388 | L |
| Sn | 1.73 | 0.29 | 0.63 | 61255 | 0.0410942 | L |
| Total | 100.00 | 100.00 | | | | |

Example 4

In another example, an experiment was carried out as described above in conjunction with Example 3, but with the aluminum and alloy exposed to carbon disulfide instead of carbon dioxide. Due to its relatively low vapor pressure, the carbon disulfide readily evaporated to gas. Subsequent analysis demonstrated that both elemental carbon and sulfur were captured. Data from an EDS analysis of an area on the surface of the sample are set forth in Tables 10 and 11 below.

TABLE 10

EDS 5 kV

| Chemical formula | ms % | mol % | Sigma | Net | K ratio | Line |
|---|---|---|---|---|---|---|
| C | 6.35 | 13.61 | 0.28 | 9571 | 0.0058581 | K |
| O | 35 | 56.29 | 0.64 | 74130 | 0.1334533 | K |
| Al | 22.42 | 21.39 | 1.46 | 51614 | 0.0942123 | K |
| S* | 1.02 | 0.82 | 2.96 | 1146 | 0.0028816 | K |
| In | 35.2 | 7.89 | 36.39 | 6137 | 0.0366235 | L |
| Total | 100.00 | 100.00 | | | | |

TABLE 11

EDS 20 kV

| Chemical formula | ms % | mol % | Sigma | Net | K ratio | Line |
|---|---|---|---|---|---|---|
| C | 6.32 | 19.43 | 0.1 | 3675 | 0.0022989 | K |
| O | 13.52 | 31.21 | 0.07 | 36546 | 0.0776428 | K |
| Al | 10.25 | 14.02 | 0.07 | 78513 | 0.0552322 | K |
| S | 0.52 | 0.59 | 0.04 | 5983 | 0.0055108 | K |
| Fe | 0.43 | 0.28 | 0.13 | 2440 | 0.0066385 | K |
| Ga | 59.24 | 31.37 | 0.43 | 133109 | 0.9091763 | K |
| In | 6.13 | 1.97 | 0.13 | 47012 | 0.0807181 | L |
| Sn | 3.59 | 1.12 | 0.14 | 25052 | 0.042016 | L |
| Total | 100.00 | 100.00 | | | | |

Data from an EDS analysis of different areas of the surface of another sample from another experimental run are set forth in Tables 12 to 21 below.

TABLE 12

EDS on spot 1, 5 kV

| Chemical formula | ms % | mol % | Sigma | Net | K ratio | Line |
|---|---|---|---|---|---|---|
| C | 6.23 | 9.93 | 0.17 | 88350 | 0.02163 | K |
| O | 49.33 | 59 | 0.25 | 1550149 | 1.1162716 | K |

TABLE 12-continued

EDS on spot 1, 5 kV

| Chemical formula | ms % | mol % | Sigma | Net | K ratio | Line |
|---|---|---|---|---|---|---|
| Al | 40.42 | 28.67 | 0.7 | 1141093 | 0.8331538 | K |
| S | 4.02 | 2.4 | 1.49 | 52613 | 0.0529195 | K |
| Total | 100.00 | 100.00 | | | | |

TABLE 13

EDS on spot 1, 20 kV

| Chemical formula | ms % | mol % | Sigma | Net | K ratio | Line |
|---|---|---|---|---|---|---|
| O | 48.11 | 65.37 | 0.24 | 623814 | 0.5301247 | K |
| Al | 35.9 | 28.92 | 0.2 | 1560014 | 0.4389735 | K |
| S | 3.15 | 2.13 | 0.19 | 128745 | 0.0474332 | K |
| Ga | 9.46 | 2.95 | 2.33 | 64642 | 0.1766093 | K |
| In | 1.64 | 0.31 | 0.63 | 41074 | 0.0282089 | L |
| Sn | 1.74 | 0.32 | 0.73 | 39334 | 0.0263879 | L |
| Total | 100.00 | 100.00 | | | | |

TABLE 14

EDS on spot 2, 5 kV

| Chemical formula | ms % | mol % | Sigma | Net | K ratio | Line |
|---|---|---|---|---|---|---|
| C | 8.64 | 13.8 | 0.18 | 99581 | 0.0243797 | K |
| O | 44.35 | 53.19 | 0.26 | 1127833 | 0.8121588 | K |
| Al | 43.25 | 30.76 | 0.72 | 1010471 | 0.7377819 | K |
| S | 3.76 | 2.25 | 1.53 | 40605 | 0.0408416 | K |
| Total | 100.00 | 100.00 | | | | |

TABLE 15

EDS on spot 2, 20 kV

| Chemical formula | ms % | mol % | Sigma | Net | K ratio | Line |
|---|---|---|---|---|---|---|
| C | 12.06 | 19.43 | 0.39 | 21948 | 0.005492 | K |
| O | 45.26 | 54.74 | 0.23 | 454231 | 0.386011 | K |
| Al | 30.66 | 21.99 | 0.15 | 1268126 | 0.3568392 | K |
| S | 2.37 | 1.43 | 0.15 | 92701 | 0.0341536 | K |
| Ga | 7.31 | 2.03 | 1.88 | 45446 | 0.1241645 | K |
| In | 1.11 | 0.19 | 0.49 | 25974 | 0.0178387 | L |
| Sn | 1.24 | 0.2 | 0.57 | 26196 | 0.017574 | L |
| Total | 100.00 | 100.00 | | | | |

TABLE 16

EDS on spot 3, 5 kV

| Chemical formula | ms % | mol % | Sigma | Net | K ratio | Line |
|---|---|---|---|---|---|---|
| C | 9.71 | 15.54 | 0.18 | 123806 | 0.0303105 | K |
| O | 42.13 | 50.62 | 0.26 | 1186329 | 0.8542827 | K |
| Al | 44.03 | 31.37 | 0.7 | 1151841 | 0.8410009 | K |
| S | 4.14 | 2.48 | 1.5 | 49897 | 0.0501873 | K |
| Total | 100.00 | 100.00 | | | | |

TABLE 17

EDS on spot 3, 20 kV

| Chemical formula | ms % | mol % | Sigma | Net | K ratio | Line |
|---|---|---|---|---|---|---|
| C | 13.17 | 21.14 | 0.38 | 25020 | 0.0062609 | K |
| O | 43.74 | 52.73 | 0.23 | 446735 | 0.3796407 | K |
| Al | 31.12 | 22.24 | 0.14 | 1377246 | 0.3875444 | K |
| S | 2.64 | 1.59 | 0.14 | 109537 | 0.0403564 | K |
| Ga | 6.81 | 1.88 | 1.78 | 44710 | 0.1221543 | K |
| In | 1.16 | 0.19 | 0.47 | 28562 | 0.0196162 | L |
| Sn | 1.36 | 0.22 | 0.54 | 30379 | 0.0203805 | L |
| Total | 100.00 | 100.00 | | | | |

TABLE 18

EDS on spot 4, 5 kV

| Chemical formula | ms % | mol % | Sigma | Net | K ratio | Line |
|---|---|---|---|---|---|---|
| C | 10.26 | 16.38 | 0.18 | 140561 | 0.0344126 | K |
| O | 41.45 | 49.7 | 0.27 | 1246795 | 0.8978242 | K |
| Al | 44.68 | 31.77 | 0.72 | 1251439 | 0.9137214 | K |
| S | 3.61 | 2.16 | 1.54 | 46538 | 0.0468088 | K |
| Total | 100.00 | 100.00 | | | | |

TABLE 19

EDS on spot 4, 20 kV

| Chemical formula | ms % | mol % | Sigma | Net | K ratio | Line |
|---|---|---|---|---|---|---|
| C | 13.81 | 21.87 | 0.36 | 25193 | 0.0063042 | K |
| O | 44.86 | 53.32 | 0.23 | 426234 | 0.3622187 | K |
| Al | 30.22 | 21.3 | 0.14 | 1239007 | 0.3486451 | K |
| S | 2.34 | 1.39 | 0.14 | 90144 | 0.0332114 | K |
| Ga | 6.34 | 1.73 | 1.79 | 38378 | 0.1048536 | K |
| In | 1.03 | 0.17 | 0.47 | 23504 | 0.0161423 | L |
| Sn | 1.41 | 0.23 | 0.54 | 29072 | 0.0195032 | L |
| Total | 100.00 | 100.00 | | | | |

TABLE 20

EDS on spot 5, 5 kV

| Chemical formula | ms % | mol % | Sigma | Net | K ratio | Line |
|---|---|---|---|---|---|---|
| C | 7.49 | 12.05 | 0.19 | 73921 | 0.0180975 | K |
| O | 45.18 | 54.55 | 0.27 | 995223 | 0.7166656 | K |
| Al | 43.13 | 30.88 | 0.74 | 868759 | 0.6343126 | K |
| S | 4.2 | 2.53 | 1.59 | 39091 | 0.0393184 | K |
| Total | 100.00 | 100.00 | | | | |

TABLE 21

EDS on spot 5, 20 kV

| Chemical formula | ms % | mol % | Sigma | Net | K ratio | Line |
|---|---|---|---|---|---|---|
| O | 42.67 | 61.46 | 0.21 | 355642 | 0.3022288 | K |
| Al | 36.22 | 30.93 | 0.17 | 990916 | 0.2788346 | K |
| S | 2.79 | 2 | 0.17 | 74913 | 0.0275999 | K |
| Ga | 14.95 | 4.94 | 1.92 | 69255 | 0.1892149 | K |

TABLE 21-continued

EDS on spot 5, 20 kV

| Chemical formula | ms % | mol % | Sigma | Net | K ratio | Line |
|---|---|---|---|---|---|---|
| In | 1.57 | 0.32 | 0.53 | 26322 | 0.0180777 | L |
| Sn | 1.79 | 0.35 | 0.61 | 27198 | 0.018246 | L |
| Total | 100.00 | 100.00 | | | | |

Figure 8:
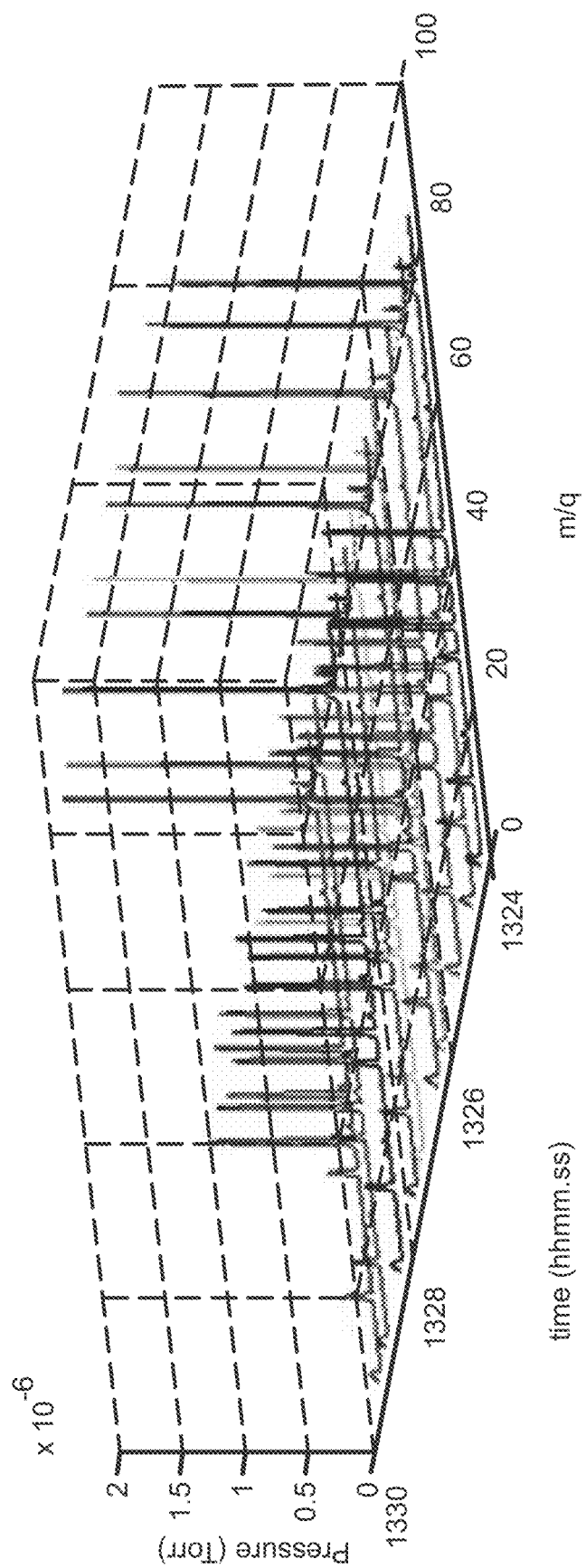
FIG. 8 is a set of mass spectra obtained as a function of time for a sample in accordance with another experiment.

FIG. 8 contains mass spectra obtained as a function of time from one of the samples. In this example, there were no new gases generated and the spectra therefore remained unchanged over time. The sample from this experiment was further analyzed using scanning electron microscope/energy-dispersive X-ray spectroscopy (SEM/EDAX) and showed significant quantities of sulfur.

Example 5

Figure 9:
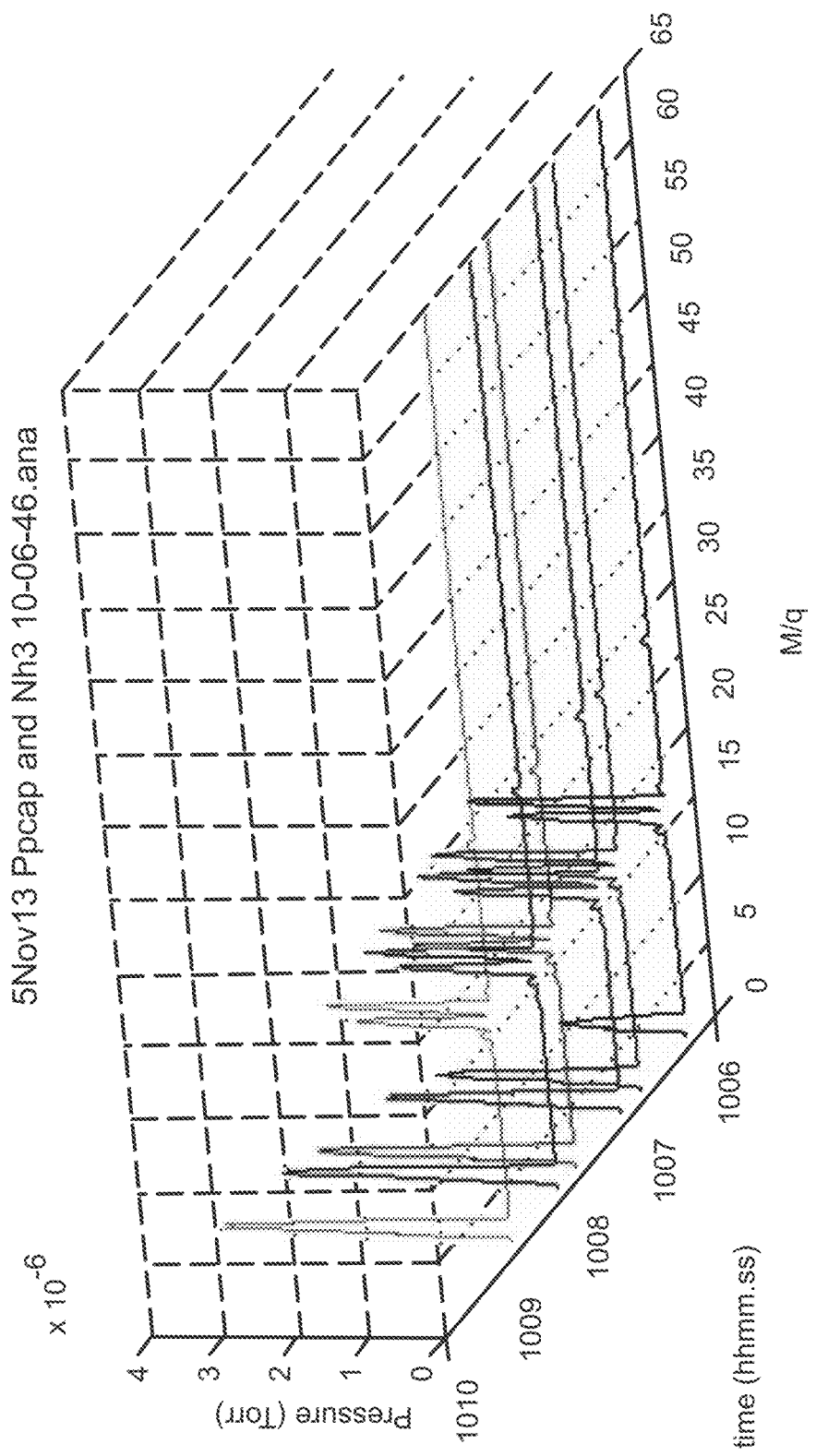
FIG. 9 is a set of mass spectra obtained as a function of time for a sample in accordance with another experiment.

In another example, an experiment was carried out as described above in conjunction with Example 3, but with the aluminum and alloy exposed to ammonia instead of carbon dioxide. Specifically, the reaction chamber was purged with ammonia gas and then sealed. FIG. 9 contains the mass spectra obtained as a function of time. Peaks around mass/charge (m/q) 17 were due to ammonia which remained relatively constant during the experiment. The peak at m/q 2 due to hydrogen increased during the few minutes of the experiment indicative of reduction of ammonia and formation of $H_2$ gas. The aluminum sample from this experiment was further analyzed using SEM/EDAX and found to contain nitrogen from the reduction of ammonia. TABLE 22 below provides data acquired from an EDS analysis on the aluminum sample taken at an acceleration voltage of 20 kV.

TABLE 22

| Chemical formula | ms % | mol % | Sigma | Net | K ratio | Line |
|---|---|---|---|---|---|---|
| C | 6.07 | 9.09 | 0.19 | 30110 | 0.0121644 | K |
| N* | 5.53 | 7.10 | 0.55 | 19725 | 0.0631765 | K |
| O | 54.49 | 61.23 | 0.32 | 524978 | 0.6238260 | K |
| Al | 33.91 | 22.59 | 0.87 | 293327 | 0.3534125 | K |
| Total | 100.00 | 100.00 | | | | |

The nitrogen found in the alloy was presumably in the form of AlN. Thus, it is believed that the method disclosed herein may be utilized to produce high-purity AlN, as well as high-purity diatomic hydrogen gas. While this Example involved the reaction of Al* with ammonia gas, it is believed that Al* would likewise be able to react with liquid ammonia and achieve similar results.

Example 6

In another example, carbon was captured from breath exhaled by a person. Aluminum was placed in contact with a Ga/In/Sn alloy in a petri dish. After breathing onto the sample, the sample was immediately analyzed by EDS. Data from the EDS analysis on different areas of the surfaces of two samples and at different acceleration voltages are set forth in Tables 23 to 28 below. It will be noted that the concentration of $CO_2$ in the air is about 0.038% and in the exhaled breath it is about 4%.

TABLE 23

EDS, Sample 1, Spot 1; 15 kV; 150x magnification

| Chemical formula | ms % | mol % | Sigma | Net | K ratio | Line |
|---|---|---|---|---|---|---|
| C | 2.57 | 4 | 0.14 | 3447 | 0.0008438 | K |
| O | 59.49 | 69.65 | 0.21 | 171310 | 0.1233614 | K |
| Al | 37.95 | 26.34 | 0.61 | 92729 | 0.0677049 | K |
| Total | 100.00 | 100.00 | | | | |

TABLE 24

EDS, Sample 2, Spot 1; 5 kV; 150x magnification

| Chemical formula | ms % | mol % | Sigma | Net | K ratio | Line |
|---|---|---|---|---|---|---|
| C* | 1.06 | 1.78 | 0.21 | 18745 | 0.0045893 | K |
| O | 51.6 | 65.29 | 0.3 | 2064429 | 1.4866077 | K |
| Na | 2.69 | 2.37 | 0.54 | 122312 | 0.079329 | K |
| Mg | 2.66 | 2.21 | 0.67 | 110023 | 0.0721005 | K |
| Al | 19.61 | 14.71 | 0.85 | 689499 | 0.5034286 | K |
| Si | 18.36 | 13.23 | 1.17 | 521243 | 0.4362127 | K |
| Hg | 4.03 | 0.41 | 8.67 | 27624 | 0.0444765 | M |
| Total | 100.00 | 100.00 | | | | |

TABLE 25

EDS, Sample 2, Spot 2; 5 kV; 150x magnification

| Chemical formula | ms % | mol % | Sigma | Net | K ratio | Line |
|---|---|---|---|---|---|---|
| C* | 1.94 | 3.05 | 0.22 | 34917 | 0.0085483 | K |
| O | 58.82 | 69.49 | 0.33 | 2302937 | 1.658358 | K |
| Al | 37.95 | 26.59 | 0.96 | 1263267 | 0.9223576 | K |
| Si | 1.29 | 0.87 | 1.36 | 33766 | 0.0282578 | K |
| Total | 100.00 | 100.00 | | | | |

TABLE 26

EDS, Sample 2, Spot 2; 20 kV; 90x magnification

| Chemical formula | ms % | mol % | Sigma | Net | K ratio | Line |
|---|---|---|---|---|---|---|
| C* | 2.96 | 5.24 | 0.37 | 10186 | 0.0025489 | K |
| O | 50.41 | 67.02 | 0.21 | 975722 | 0.8291808 | K |
| Al | 24.38 | 19.22 | 0.16 | 1665484 | 0.468652 | K |
| Si | 5.84 | 4.42 | 0.21 | 346728 | 0.1058574 | K |
| Ga | 9.01 | 2.75 | 1.85 | 101567 | 0.2774932 | K |
| In | 2.54 | 0.47 | 0.49 | 106908 | 0.073423 | L |
| Sn | 4.86 | 0.87 | 0.57 | 184887 | 0.1240342 | L |
| Total | 100.00 | 100.00 | | | | |

Example 7

Al* Matrix, Carbon Capture from Air

Figure 10:
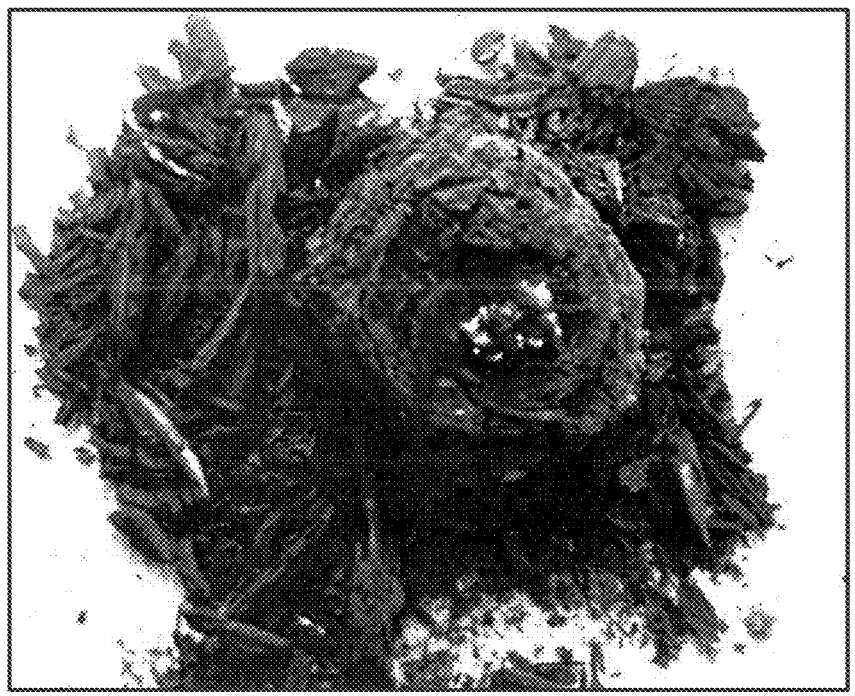
FIG. 10 is a photograph of the results of an experiment in which aluminum was placed in contact with a Ga/In/Sn alloy.
Figure 11:
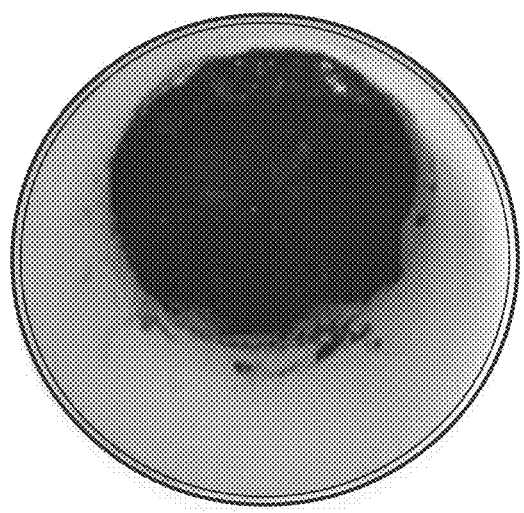
FIG. 11 is a photograph of the results of another experiment in which aluminum was placed in contact with a Ga/In/Sn alloy.

In one experiment, aluminum was placed in contact with a Ga/In/Sn alloy in a cup and left exposed to ambient air for several days. FIG. 10 is a photograph of the results of the reaction. The dark material indicates capture of carbon directly from the ambient air. In another experiment, aluminum was placed in contact with a Ga/In/Sn alloy in a cup and left exposed to ambient air for one night. As indicated by the photograph of FIG. 11, the single overnight period was sufficient for capturing carbon directly from the ambient air. The carbon content was measured up to 9.2 mol %. The carbon capture-transformation is concentrated from about 0.038% in the air to from 4% to 9% as captured-transformed, and over a longer period of time to about 24%. Data from the EDS analysis on different areas of the surfaces of two samples and at different acceleration voltages are set forth in Tables 27 to 35 below.

TABLE 27

EDS, Sample 1, Spot 1; 5 kV; 250x magnification

| Chemical formula | ms % | mol % | Sigma | Net | K ratio | Line |
|---|---|---|---|---|---|---|
| C* | 2.43 | 3.86 | 0.18 | 14893 | 0.0036462 | K |
| O | 56.03 | 66.78 | 0.26 | 752013 | 0.5415291 | K |
| Al | 41.54 | 29.36 | 0.76 | 478526 | 0.3493894 | K |
| Total | 100.00 | 100.00 | | | | |

TABLE 28

EDS, Sample 1, Spot 1; 5 kV; 1100x magnification

| Chemical formula | ms % | mol % | Sigma | Net | K ratio | Line |
|---|---|---|---|---|---|---|
| C* | 2.16 | 3.47 | 0.19 | 13347 | 0.0032676 | K |
| O | 54.53 | 65.62 | 0.28 | 744921 | 0.536422 | K |
| Al | 43.31 | 30.91 | 0.8 | 510078 | 0.3724265 | K |
| Total | 100.00 | 100.00 | | | | |

TABLE 29

EDS, Sample 2, Spot 1; 20 kV; 250x magnification

| Chemical formula | ms % | mol % | Sigma | Net | K ratio | Line |
|---|---|---|---|---|---|---|
| C* | 3.13 | 6.62 | 0.19 | 11236 | 0.0028115 | K |
| O | 39.45 | 62.71 | 0.16 | 563082 | 0.4785142 | K |
| Al | 20.68 | 19.5 | 0.12 | 1066379 | 0.3000692 | K |
| Ga | 21.5 | 7.85 | 1.06 | 229913 | 0.6281521 | K |
| In | 7.29 | 1.62 | 0.29 | 285997 | 0.1964196 | L |
| Sn | 7.94 | 1.7 | 0.33 | 281854 | 0.1890862 | L |
| Total | 100.00 | 100.00 | | | | |

TABLE 30

EDS, Sample 1, Spot 2; 5 kV; 250x magnification

| Chemical formula | ms % | mol % | Sigma | Net | K ratio | Line |
|---|---|---|---|---|---|---|
| C* | 2.62 | 4.17 | 0.17 | 31663 | 0.0077517 | K |
| O | 54.89 | 65.68 | 0.24 | 1460745 | 1.0518907 | K |
| Al | 42.5 | 30.15 | 0.7 | 975086 | 0.7119458 | K |
| Total | 100.00 | 100.00 | | | | |

TABLE 31

EDS, Sample 1, Spot 2; 20 kV; 250x magnification

| Chemical formula | ms % | mol % | Sigma | Net | K ratio | Line |
|---|---|---|---|---|---|---|
| C* | 4.71 | 9.25 | 0.24 | 11646 | 0.0029143 | K |
| O | 42.46 | 62.62 | 0.18 | 440761 | 0.3745643 | K |
| Al | 22.28 | 19.48 | 0.14 | 835733 | 0.2351676 | K |
| Ga | 18.15 | 6.14 | 1.3 | 133063 | 0.3635453 | K |
| In | 6.42 | 1.32 | 0.35 | 174386 | 0.1197661 | L |
| Sn | 5.99 | 1.19 | 0.4 | 147051 | 0.0986518 | L |
| Total | 100.00 | 100.00 | | | | |

TABLE 32

EDS, Sample 2, Spot 1; 5 kV; 250x magnification

| Chemical formula | ms % | mol % | Sigma | Net | K ratio | Line |
|---|---|---|---|---|---|---|
| C* | 1.47 | 2.89 | 0.12 | 15127 | 0.0037035 | K |
| Al | 31.72 | 27.71 | 0.59 | 543909 | 0.3971276 | K |
| In | 11.43 | 2.35 | 15.1 | 14560 | 0.0347531 | L |
| Sn | 11.39 | 2.26 | 23.36 | 9545 | 0.0233658 | L |
| Total | 100.00 | 100.00 | | | | |

TABLE 33

EDS, Sample 2, Spot 1; 20 kV; 250x magnification

| Chemical formula | ms % | mol % | Sigma | Net | K ratio | Line |
|---|---|---|---|---|---|---|
| C* | 2.24 | 5.54 | 0.17 | 7180 | 0.0017966 | K |
| O | 29.18 | 54.25 | 0.13 | 395998 | 0.3365239 | K |
| Al | 20.13 | 22.2 | 0.1 | 934319 | 0.2629087 | K |
| Ga | 32.97 | 14.07 | 0.83 | 357153 | 0.9757885 | K |
| In | 7.74 | 2.01 | 0.23 | 298254 | 0.2048375 | L |
| Sn | 7.74 | 1.94 | 0.26 | 270715 | 0.1816134 | L |
| Total | 100.00 | 100.00 | | | | |

TABLE 34

EDS, Sample 2, Spot 2; 5 kV; 250x magnification

| Chemical formula | ms % | mol % | Sigma | Net | K ratio | Line |
|---|---|---|---|---|---|---|
| C* | 4.55 | 9.27 | 0.22 | 15415 | 0.0038574 | K |
| O | 40.33 | 61.63 | 0.17 | 557381 | 0.4736692 | K |
| Al | 21.01 | 19.03 | 0.13 | 1044037 | 0.2937823 | K |
| Ga | 20.74 | 7.27 | 1.2 | 209507 | 0.5724009 | K |
| In | 6.74 | 1.44 | 0.32 | 250806 | 0.1722506 | L |
| Sn | 6.62 | 1.36 | 0.37 | 222910 | 0.1495425 | L |
| Total | 100.00 | 100.00 | | | | |

TABLE 35

EDS, Sample 2, Spot 2; 20 kV; 250x magnification

| Chemical formula | ms % | mol % | Sigma | Net | K ratio | Line |
|---|---|---|---|---|---|---|
| C* | 1.79 | 3.44 | 0.13 | 34904 | 0.0085453 | K |
| O | 45.48 | 65.49 | 0.25 | 1515589 | 1.0913848 | K |
| Al | 31.48 | 26.88 | 0.63 | 1023275 | 0.7471302 | K |
| In | 10.53 | 2.11 | 16.16 | 25364 | 0.0605426 | L |

TABLE 35-continued

| EDS, Sample 2, Spot 2; 20 kV; 250x magnification | | | | | | |
|---|---|---|---|---|---|---|
| Chemical formula | ms % | mol % | Sigma | Net | K ratio | Line |
| Sn | 10.73 | 2.08 | 25 | 17001 | 0.0416161 | L |
| Total | 100.00 | 100.00 | | | | |

Example 8

Al/Mg Alloy Dissolved in Matrix Alloy Reacted in Water

The tops (Al~95.5%, Mg~4.5%) of soda drink containers were dissolved in a Ga/In/Sn alloy by rubbing only a small amount of the ternary alloy on to the Al/Mg alloy. The matrix was then placed in a container of water, producing a gray solid product. It is postulated that this experiment demonstrates that highly pure (>99%) aluminum is not required as a source of aluminum to be activated by the Ga/In/Sn alloy.

Example 9

Reactivity of Activated Al* with Hydrocarbons

In this Example, the objective was to determine whether Activated Al* would react with methane or other hydrocarbon during the process or removing impurities such as sulfur compounds from the methane or other hydrocarbon. Hexane was selected as the hydrocarbon example and carbon disulfide was selected as the target sulfur source. At the time of the initiation of the experiment, it was experimentally unverified whether or not Activated Al* would react with methane or hexane. From theory, because methane is non-polar it would not be expected to react. Using hexane as a surrogate substitute for other non-polar hydrocarbons, a similar result could be expected. The preliminary test results are as follows.

Figure 12:
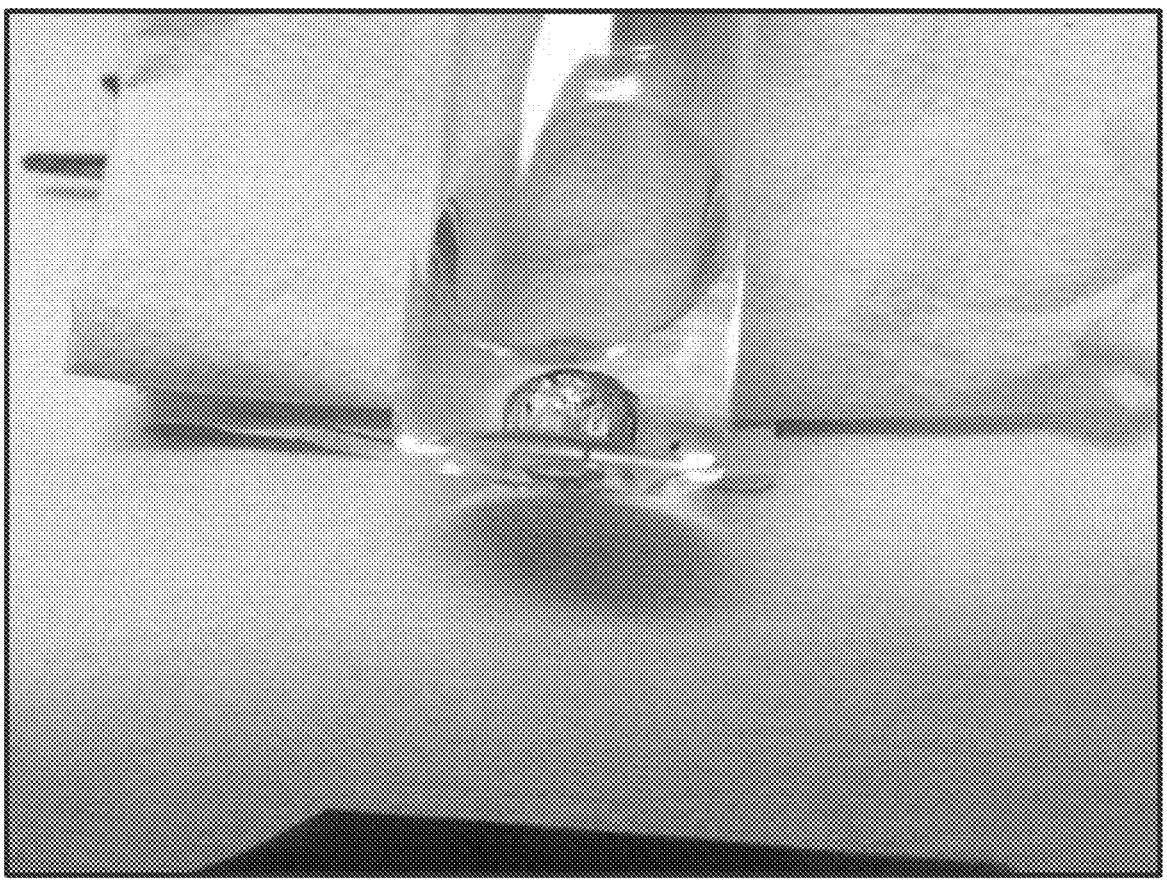
FIG. 12 is a photograph of the results of an experiment in which aluminum was activated in a Ga/In/Sn alloy and placed in a container containing hexane.

Referring to the photograph of FIG. 12, aluminum was activated in a Ga/In/Sn alloy and placed in a container containing hexane. As shown, after twenty-four hours there was no evidence of a reaction of the activated aluminum with hexane.

Figure 13:
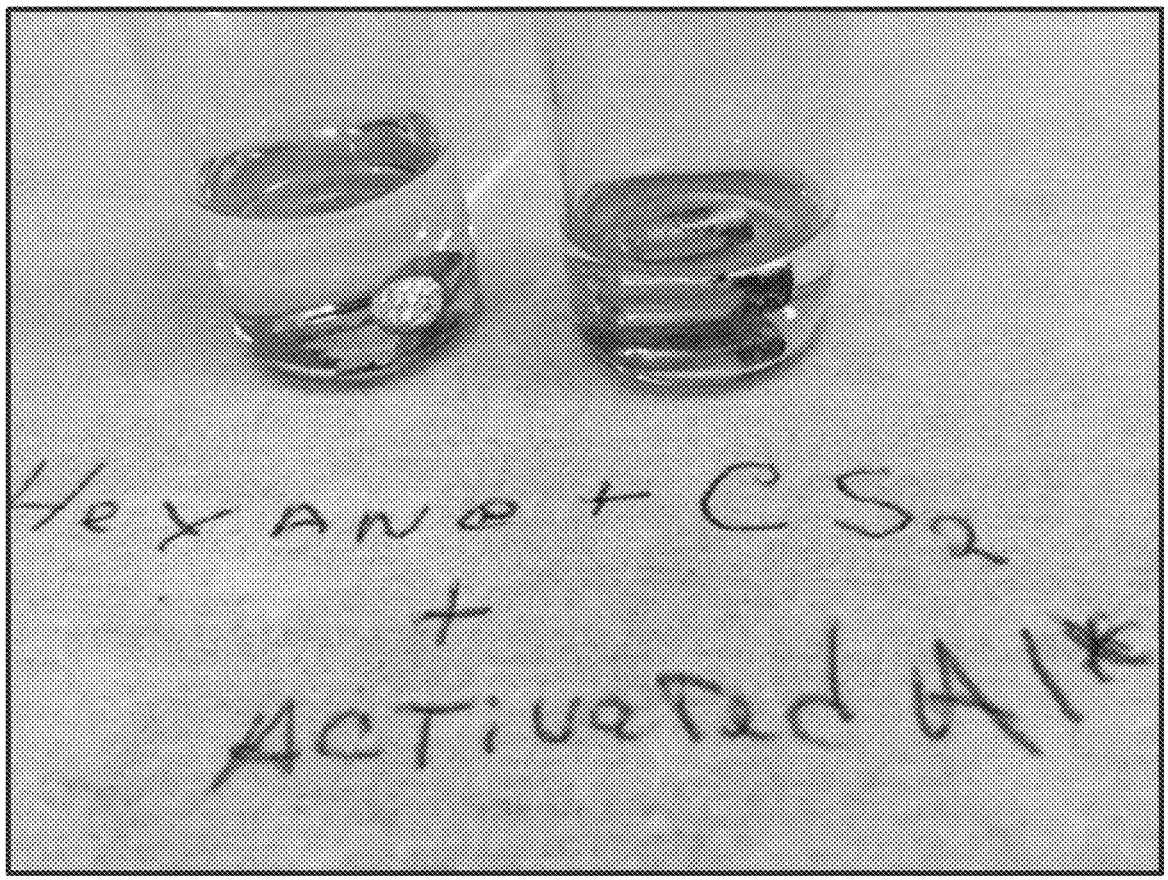
FIG. 13 is a photograph of the results of an experiment in which two samples of aluminum were activated in a Ga/In/Sn alloy, then placing the resulting activated aluminum/alloy matrix samples in respective containers containing hexane, with about three drops of carbon disulfide added to the left container and about ten drops of carbon disulfide added to the right container.

Referring to the photograph of FIG. 13, two samples of aluminum were activated in a Ga/In/Sn alloy by rubbing each sample into the alloy until the alloy wetted the surface of the alloy. Each activated aluminum/alloy matrix was then placed in a respective container containing hexane. Also, about three drops of carbon disulfide were added to the left container, and about ten drops of carbon disulfide were added to the right container. The containers were then left overnight. The photograph of FIG. 13, taken the following day, clearly shows dark areas on the surface.

Figure 14:
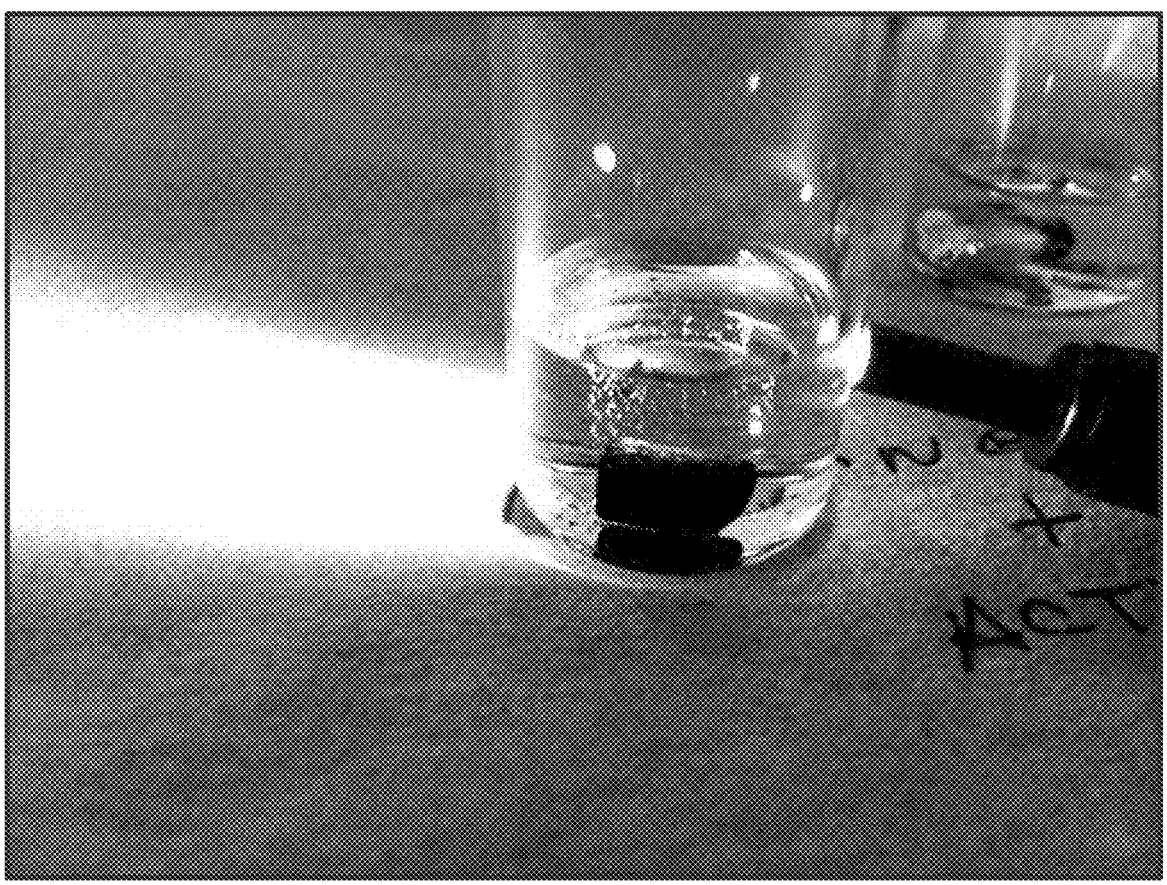
FIG. 14 is a photograph of the sample from the left container shown in FIG. 13.

FIG. 14 is a photograph of the sample from the left container shown in FIG. 13. It was observed that the sample started to change color to a dark shade, and that a translucent to transparent material was growing out from the surface of the sample. It is noted that $Al_2S_3$ is a transparent solid.

Example 10

Al* Matrix, Carbon Capture from Carbonated Water

In one experiment, activated aluminum was prepared by dissolving about 5 cc of aluminum in a Ga/In/Sn alloy, which was then added to about 30 cc of deionized water that was carbonated ($CO_2$ was dissolved in the water). The reaction (proceeding at room temperature) was immediately vigorous and produced large, uniform iridescent flakes. The reaction yielded back the Ga/In/Sn alloy, which no longer was reacting because most of or the entire activated aluminum had been reacted at that point.

In a subsequent experiment, two samples of activated aluminum were prepared as just described. One sample was placed in carbonated water while the other sample was placed in pure water, both at room temperature. Both the carbonated water and pure water samples were examined side-by-side and both proceeded as predicted with violent bubbling, producing hydrogen and a white precipitate. The pure water sample's precipitate was fine in texture while the carbonated water sample's precipitate was flocculent. The precipitate when dried looked white and "pearlescent" for the $CO_2/H_2O$ sample. The underside of the activated Al* metal matrix was black under the metal alloy ball. It is postulated that under controlled conditions of limiting access to oxidation and confining the liberating hydrogen with the reduction of the $CO_2$, it is possible to provide a reducing environment for the production of carbonaceous materials. In accordance with the Gibbs free energy of formation, where two or more reactions are possible, the reaction path will follow a dominant path as prescribed by reaction conditions. For example, by changing the ratio of $CO_2$ to $H_2O$ with pressure, temperature and pH of the solution, one reaction path can be made preferable over the other.

Figure 15:
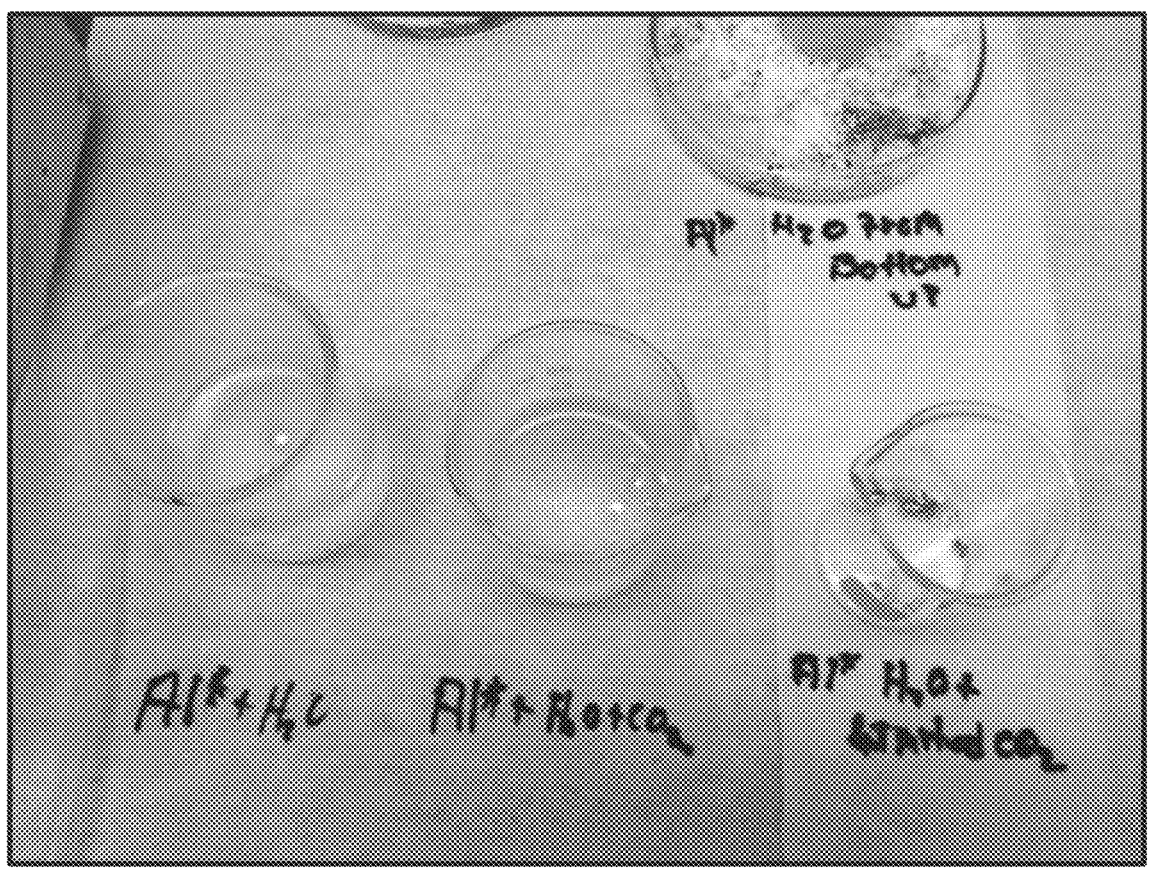
FIG. 15 is a photograph showing the results of reacting the activated Al* with pure water (left) and carbonated water (right).
Figure 16:
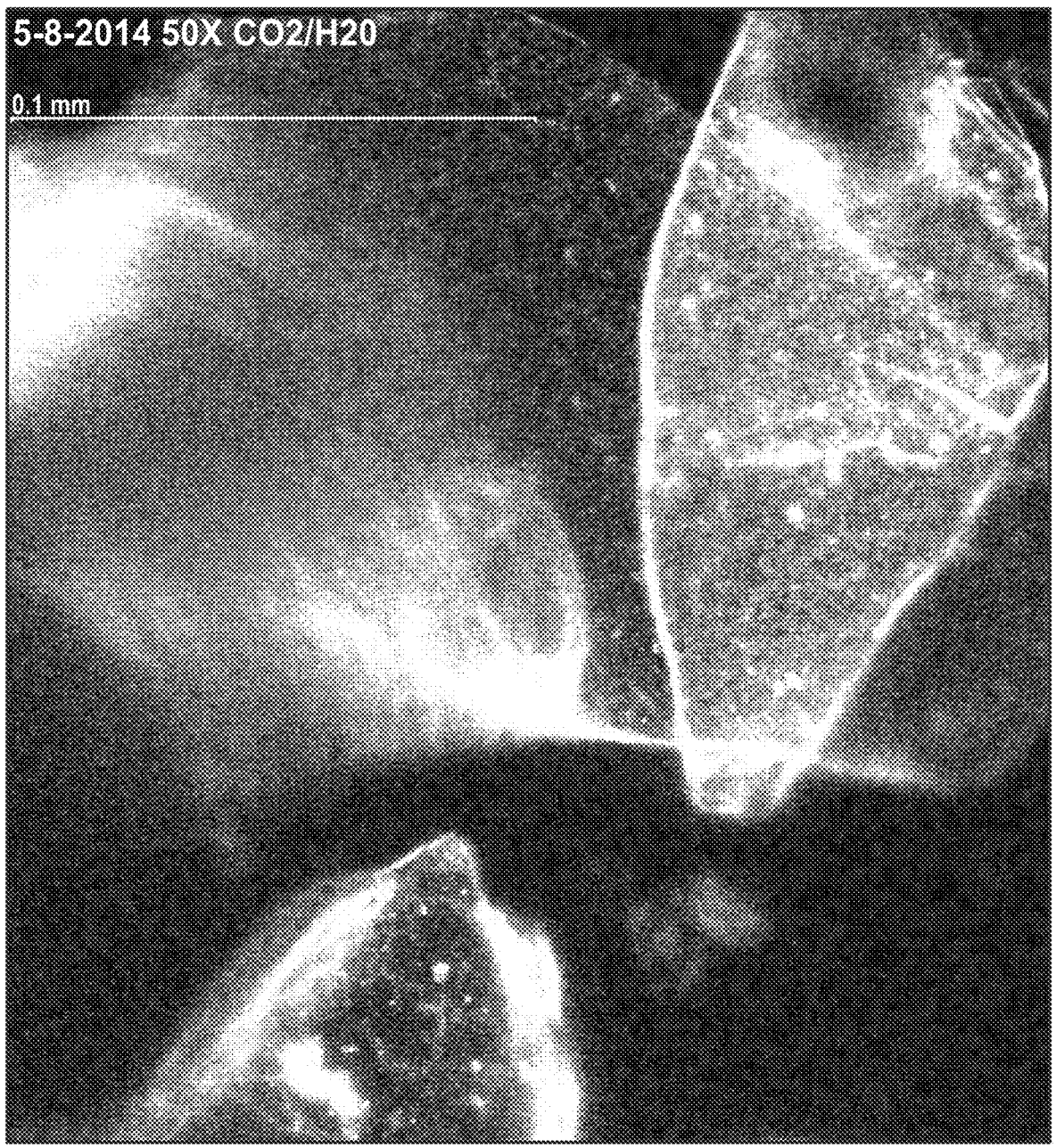
FIG. 16 is a photograph showing "pearlescent" flakes produced from the $CO_2/H_2O$ reaction with Al* in conjunction with the experiment of FIG. 15.
Figure 17:
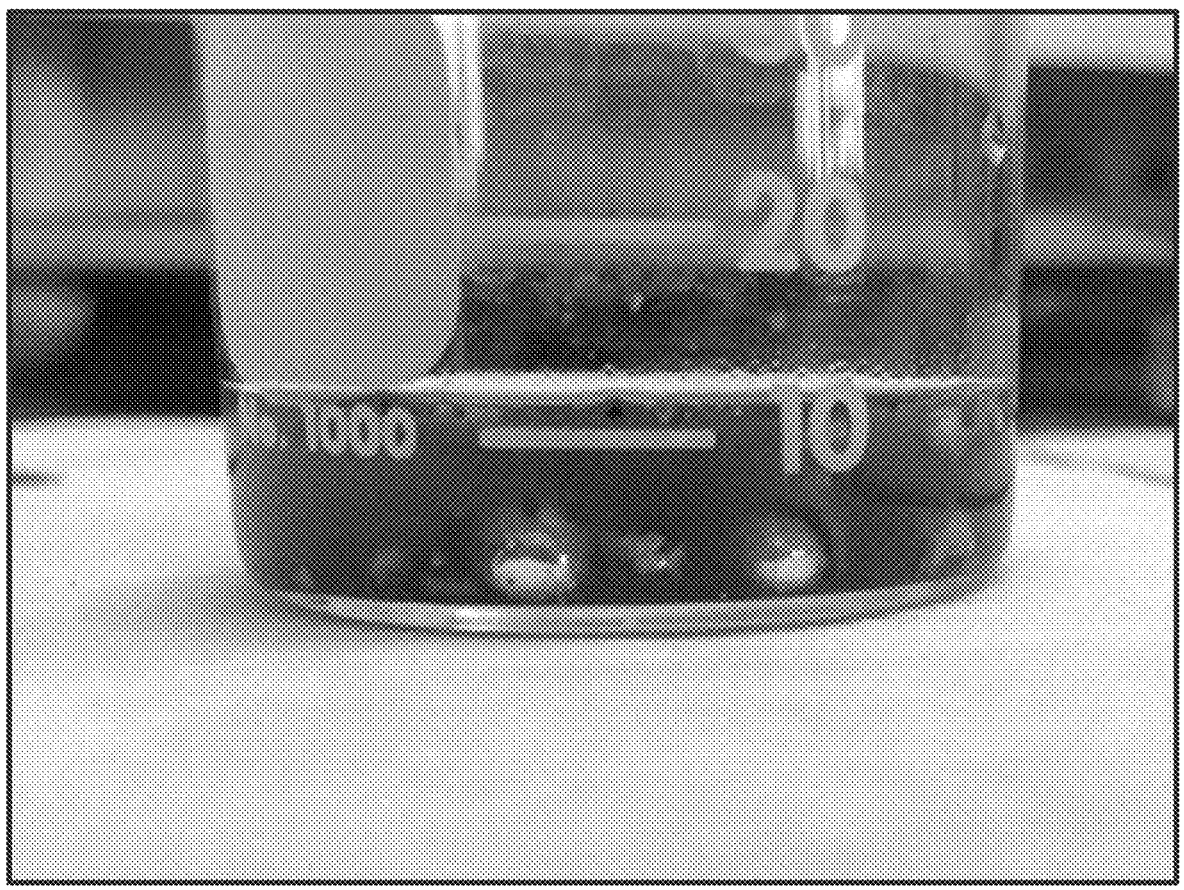
FIG. 17 is a photograph showing the beaker in which the reaction between $CO_2/H_2O$ and Al* was carried out in conjunction with the experiment of FIG. 15.

FIG. 15 is a photograph showing the results of reacting the activated Al* with pure water (left) and carbonated water (right). FIG. 16 is a photograph showing the "pearlescent" flakes produced from the $CO_2/H_2O$ reaction with Al*. FIG. 17 is a photograph showing the beaker in which the reaction between $CO_2/H_2O$ and Al* was carried out. It is observed that iridescent whitish flakes cover the surface of the balled up activated Al* alloy matrix, and the surface underneath the ball is black.

Example 11

Activated Calcium Reactions with Water and Carbonated Water

Calcium beads were contacted with a Ga/In/Sn alloy and added to water. The calcium reacted with the water and formed calcium oxide (CaO), which then formed calcium hydroxide, $Ca(OH)_2$. Carbonated water was then added, resulting in the formation of calcium carbonate ($CaCO_3$). It is believed that activated calcium Ca* will react with $CO_2$ (gas or liquid) to form CaO, and after adding carbonated water will again react to form the carbonate, thus providing two pathways for capturing carbon.

Example 12

Activated Calcium Reactions with Air

Similar to Example 7 involving activated aluminum, calcium beads were contacted with a Ga/In/Sn alloy and left exposed to ambient air. Like activated aluminum, the activated calcium was able to capture carbon directly from the ambient air. The carbon content was measured up to about 8 mol %. Data from the EDS analysis on the surfaces of two samples and at different acceleration voltages are set forth in Tables 36 to 39 below.

TABLE 36

EDS, Pellet 1; 5 kV

| Chemical formula | ms % | mol % | Sigma | Net | K ratio | Line |
|---|---|---|---|---|---|---|
| C | 3.98 | 7.4 | 0.06 | 237181 | 0.0580672 | K |
| O | 46.66 | 65.1 | 0.21 | 2734978 | 1.9694734 | K |
| Ca | 49.36 | 27.49 | 8.53 | 257377 | 0.6089488 | K |
| Total | 100.00 | 100.00 | | | | |

TABLE 37

EDS, Pellet 1; 20 kV

| Chemical formula | ms % | mol % | Sigma | Net | K ratio | Line |
|---|---|---|---|---|---|---|
| C | 4.63 | 8.02 | 0.07 | 45398 | 0.0113601 | K |
| O | 54.28 | 70.64 | 0.31 | 370553 | 0.3149005 | K |
| Ca | 41.09 | 21.35 | 0.12 | 2886694 | 1.3834229 | K |
| Total | 100.00 | 100.00 | | | | |

TABLE 38

EDS, Pellet 2; 5 kV

| Chemical formula | ms % | mol % | Sigma | Net | K ratio | Line |
|---|---|---|---|---|---|---|
| C | 3.36 | 6.2 | 0.06 | 189672 | 0.0464359 | K |
| O | 48.41 | 67.11 | 0.21 | 2728950 | 1.9651325 | K |
| Ca | 48.24 | 26.69 | 8.6 | 238917 | 0.5652716 | K |
| Total | 100.00 | 100.00 | | | | |

TABLE 39

EDS, Pellet 2; 20 kV

| Chemical formula | ms % | mol % | Sigma | Net | K ratio | Line |
|---|---|---|---|---|---|---|
| C | 4.25 | 7.36 | 0.07 | 44719 | 0.0111901 | K |
| O | 54.86 | 71.26 | 0.32 | 425058 | 0.3612196 | K |
| Al | 0.74 | 0.57 | 0.09 | 51709 | 0.0145505 | K |
| Ca | 40.15 | 20.82 | 0.12 | 3115214 | 1.492939 | K |
| Total | 100.00 | 100.00 | | | | |

Figure 18:
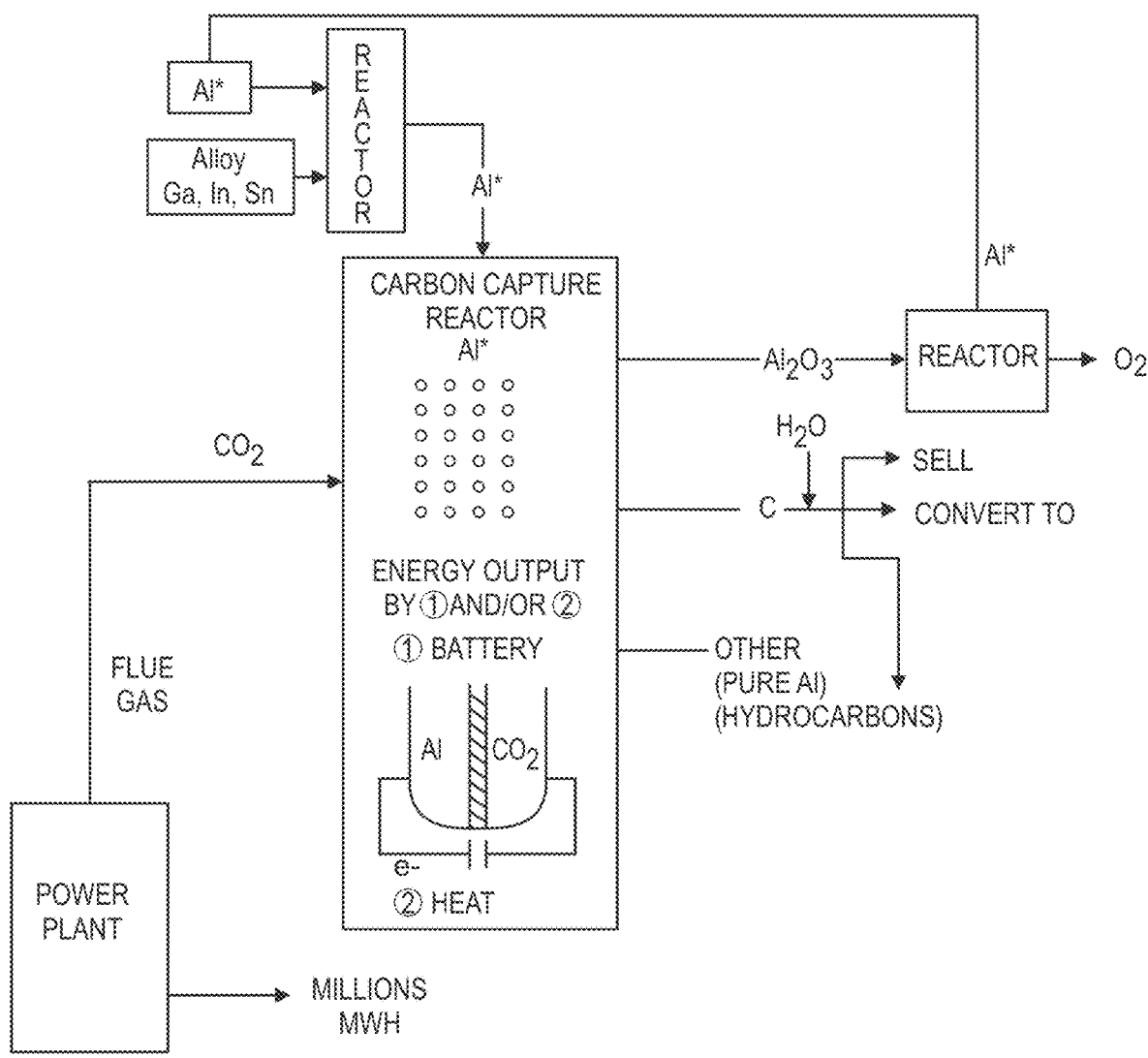
FIG. 18 is a schematic view of an example of a system for capturing a target element from a target source according to some embodiments.

FIG. 18 is a schematic view of an example of a system for capturing a target element from a target source according to some embodiments. FIG. 18 may also be considered as a process flow diagram descriptive of the method implemented by the system. The specific example of FIG. 18 is directed to the capture of carbon from flue gas, with the understanding that the system may be configured for capture of other target elements from other types of target sources as described herein. As shown, aluminum and a suitable aluminum activating agent (a ternary alloy in the illustrated example) are introduced into a reactor whereby an activated aluminum (Al*) is produced, as described elsewhere in the present disclosure. In the present example, the matrix is a liquid metal alloy (Al*/Ga/In/Sn) that is then introduced into another reactor ("carbon capture reactor"). Flue gas (containing carbon dioxide) outputted from a power plant or other source is introduced into the carbon capture reactor by any suitable means. The carbon dioxide reacts with the activated aluminum to liberate carbon as described elsewhere in the present disclosure. The liberated carbon may then be collected and utilized for any purpose such as, for example, the synthesis of chemical compounds, the fabrication of structures or devices, etc. In one example, as shown and as described elsewhere in the present disclosure, the carbon may be reacted with a hydrogen source to produce one or more types of hydrocarbons or other organic compounds (e.g., alcohols, ketones, etc.). As also shown in FIG. 18 and as described elsewhere in the present disclosure, aluminum may be recovered from aluminum compounds produced from the process for re-use in the system/process. In the illustrated example, aluminum oxide is introduced in a reactor configured for carrying out a reduction reaction that produces aluminum and diatomic oxygen gas.

As also shown in FIG. 18, the carbon capture reactor (or a separate reactor associated with the carbon capture reactor) may be further configured for harvesting the energy of the exothermic reaction between the carbon dioxide and the activated aluminum. For example, the reactor may include an $Al/CO_2$ battery that generates electrical current. Such a battery may operate in a manner analogous to an Al/air battery. Alternatively or additionally, the carbon capture reactor may be configured for converting the heat of reaction from the carbon dioxide and activated aluminum to a useful form of energy, which may be achieved by various means as appreciated by persons skilled in the art.

It will be appreciated that the system of FIG. 18 may alternatively utilize activated metals other than activated aluminum, as described above.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A method for capturing a target element from a target source, the method comprising:
   providing a matrix comprising an activated metal consisting essentially of aluminum dispersed in a metal activating agent, by contacting a solid metal to be activated with the metal activating agent, and maintaining contact between the solid metal and the metal activating agent for a period of time sufficient for metal atoms from the solid metal to disperse in the metal activating agent, wherein the metal activating agent is selected from the group consisting of gallium, indium, tin, and a combination of two or more of the foregoing; and
   contacting the target source with the matrix, wherein:
   the target element is selected from the group consisting of carbon, sulfur, nitrogen, and a combination of two or more of the foregoing;
   the target source comprises a compound selected from the group consisting of a target carbon compound, a target sulfur compound, a target nitrogen compound, and a combination of two or more of the foregoing; and
   the activated metal reacts with the target source to produce a product selected from the group consisting of elemental carbon, elemental sulfur, elemental nitrogen, a transformed carbon compound transformed from the target carbon compound, a transformed sulfur compound transformed from the target sulfur compound, a transformed nitrogen compound transformed from the target nitrogen compound, and a combination of two or more of the foregoing.

2. The method of claim 1, wherein the activated metal reacts with the target source to produce at least one of the transformed carbon compound, the transformed sulfur compound, and the transformed nitrogen compound, and further comprising:
producing at least one of elemental carbon from the transformed carbon compound, elemental sulfur from the transformed sulfur compound, and elemental nitrogen from the transformed nitrogen compound.

3. The method of claim 2, wherein producing at least one of elemental carbon from the transformed carbon compound, elemental sulfur from the transformed sulfur compound, and elemental nitrogen from the transformed nitrogen compound comprises reacting the activated metal with at least one of the transformed carbon compound, the transformed sulfur compound, and the transformed nitrogen compound.

4. The method of claim 1, wherein the activated metal consists essentially of an aluminum alloy.

5. The method of claim 1, wherein the activated metal reacts with the target source to produce a metal compound, and further comprising recovering metal from the produced metal compound and producing additional activated metal from the recovered metal.

6. The method of claim 1, wherein the target source comprises a carbon compound, and contacting the target source with the matrix is done in the presence of a hydrogen source, and further comprising producing an organic compound.

7. The method of claim 1, wherein the solid metal has a form selected from the group consisting of a rod, a plate, a container, a pellet, a powder, and a combination of two or more of the foregoing.

8. The method of claim 1, wherein maintaining contact causes metal atoms to diffuse into the metal activating agent, or the metal activating agent to diffuse into the solid metal, or both of the foregoing.

9. The method of claim 1, wherein contacting the solid metal with the metal activating agent comprises placing the solid metal and the metal activating agent in a container.

10. The method of claim 9, wherein the container is composed of the same metal as the activated metal.

11. The method of claim 1, wherein contacting the metal with the metal activating agent comprises coating the metal with the metal activating agent or coating the metal activating agent with the metal.

12. The method of claim 1, comprising forming the solid metal as a coating on a substrate.

13. The method of claim 1, comprising replenishing the matrix with activated metal by bringing additional solid metal into contact with the metal activating agent.

14. The method of claim 13, comprising contacting an additional amount of the target source with the replenished matrix.

15. The method of claim 1, wherein providing the matrix comprises applying the matrix as a coating on a substrate.

16. The method of claim 1, wherein the metal activating agent is substantially inert to the activated metal, the target compound, and products of the reaction between the activated metal and the target compound.

17. The method of claim 1, wherein contacting the target source with the matrix is done in the presence of a hydrogen source, and while the activated metal reacts with the target source, further comprising generating hydrogen gas, generating a hydrogen compound, or generating both hydrogen gas and a hydrogen compound.

18. The method of claim 17, wherein the hydrogen source is water, alcohol, or both water and alcohol.

19. The method of claim 1, wherein the activated metal reacts with the target source to produce at least one of a metal compound and an alkylated compound.

20. The method of claim 1, wherein the activated metal reacts with the target source to produce a metal compound selected from the group consisting of metal oxide, metal hydroxide, metal carbide, metal sulfide, and metal nitride.

21. The method of claim 1, wherein the metal activating agent is in a liquid state, a flowable state, or a solid state.

22. The method of claim 1, wherein contacting the target source with the matrix is done while the concentration of activated metal in the matrix is in a range from about 0.01% to about 50% by weight.

23. The method of claim 1, wherein contacting the target source with the matrix is done at a process temperature in a range from 7° C. to 400° C.

24. The method of claim 1, wherein contacting the target source with the matrix is done at about room temperature, at about atmospheric pressure, or at both of the foregoing.

25. The method of claim 1, comprising replenishing the matrix with unreacted metal.

26. The method of claim 25, comprising contacting an additional amount of the target source with the replenished matrix.

27. The method of claim 1, wherein contacting the target source with the matrix comprises flowing the target source into contact with the matrix.

28. The method of claim 1, wherein the target source is a liquid, a gas, a supercritical fluid, a solid, or a solid dispersion phase.

29. The method of claim 1, wherein the target compound is selected from the group consisting of carbon dioxide, sulfur dioxide, sulfur trioxide, carbon disulfide, hydrogen sulfide, thiofuran, thiophenes, mercaptans, ammonia, nitric oxide, nitrogen dioxide, and a combination of two or more of the foregoing.

30. The method of claim 1, wherein the target source comprises a thiophene, or a mixture of a thiophene and one or more of a hydrocarbon and an alcohol.

31. The method of claim 1, wherein the target source comprises a hydrocarbon, or a mixture of a hydrocarbon and one or more of water, a hydrated compound, an alcohol, and a compound including a hydroxyl functional group (—OH).

32. The method of claim 1, wherein the target source comprises a mixture selected from the group consisting of air, products of combustion, products of fermentation, products of biodegradation, products of ammonia synthesis, products of natural gas extraction, and a combination of two or more of the foregoing.

33. The method of claim 1, wherein the matrix is provided in a container.

34. The method of claim 33, wherein the container is composed of the same metal as the activated metal.

35. The method of claim 1, wherein contacting the target source with the matrix is done under a condition selected from the group consisting of: while the container is open to ambient; and while the container is closed.

36. A method for capturing a target element from a target source, the method comprising:
providing a matrix comprising an activated metal consisting essentially of magnesium dispersed in a metal activating agent, by contacting a solid metal to be activated with the metal activating agent, and maintaining contact between the solid metal and the metal activating agent for a period of time sufficient for metal atoms from the solid metal to disperse in the metal activating agent, wherein the metal activating agent is selected from the group consisting of gallium, indium, tin, and a combination of two or more of the foregoing; and contacting the target source with the matrix, wherein:

the target element is selected from the group consisting of carbon, sulfur, nitrogen, and a combination of two or more of the foregoing;

the target source comprises a compound selected from the group consisting of a target carbon compound, a target sulfur compound, a target nitrogen compound, and a combination of two or more of the foregoing; and the activated metal reacts with the target source to produce a product selected from the group consisting of elemental carbon, elemental sulfur, elemental nitrogen, a transformed carbon compound transformed from the target carbon compound, a transformed sulfur compound transformed from the target sulfur compound, a transformed nitrogen compound transformed from the target nitrogen compound, and a combination of two or more of the foregoing.

* * * * *